(12) United States Patent
Hampson et al.

(10) Patent No.: US 9,782,409 B2
(45) Date of Patent: Oct. 10, 2017

(54) TREATMENT OF CANCER AND BENIGN PROLIFERATIVE DISORDERS

(71) Applicant: The University of Manchester, Manchester (GB)

(72) Inventors: Ian Hampson, Manchester (GB); Lynne Hampson, Manchester (GB)

(73) Assignee: The University of Manchester, Manchester (GB)

( * ) Notice: Subject to any disclaimer, the term of this patent is extended or adjusted under 35 U.S.C. 154(b) by 0 days.

(21) Appl. No.: 15/031,209

(22) PCT Filed: Oct. 23, 2014

(86) PCT No.: PCT/GB2014/053169
§ 371 (c)(1),
(2) Date: Apr. 21, 2016

(87) PCT Pub. No.: WO2015/059485
PCT Pub. Date: Apr. 30, 2015

(65) Prior Publication Data
US 2016/0271132 A1    Sep. 22, 2016

(30) Foreign Application Priority Data

Oct. 23, 2013  (GB) .................................. 1318742.2
May 27, 2014  (GB) .................................. 1409362.9

(51) Int. Cl.
| | | |
|---|---|---|
| *A61K 31/505* | (2006.01) | |
| *A61K 31/513* | (2006.01) | |
| *A61K 9/00* | (2006.01) | |
| *A61K 31/427* | (2006.01) | |
| *A61K 9/48* | (2006.01) | |

(52) U.S. Cl.
CPC .......... *A61K 31/513* (2013.01); *A61K 9/0014* (2013.01); *A61K 9/0034* (2013.01); *A61K 9/4858* (2013.01); *A61K 9/4866* (2013.01); *A61K 31/427* (2013.01); *A61K 31/505* (2013.01)

(58) Field of Classification Search
CPC ................................................... A61K 31/505
USPC ......................................................... 514/274
See application file for complete search history.

(56) References Cited

U.S. PATENT DOCUMENTS

2010/0173861 A1 *  7/2010  Huang .................. A61K 31/704
                                                              514/33

FOREIGN PATENT DOCUMENTS

WO    2005053694 A1    6/2005
WO    2015059485 A1    4/2015

OTHER PUBLICATIONS

PCT/GB2014/053169 International Search Report and Written Opinion dated Jan. 28, 2015; 11 pages.
Anonymous. Kaletra Cream Attacks HPV, May Stop Cervical Cancer. (Aug. 25, 2006). Retrieved from: http://www.natap.org/2006/HIV/082506_02.htm on Jan. 19, 2015; 3 pages.
Batman et al. Lopinavir up-regulates expression of the antiviral protein ribonuclease L in human papillomavirus-positive cervical carcinoma cells. Antiviral Therapy (2011). 16:515-525.
Zehbe et al. Lopinavir shows greater specificity than zinc finger ejecting compounds as a potential treatment for human papillomavirus-related lesions. Antiviral Research (2011). 91:161-166.

* cited by examiner

*Primary Examiner* — Raymond Henley, III
(74) *Attorney, Agent, or Firm* — Linda B. Huber; Nixon Peabody LLP

(57) ABSTRACT

Disclosed herein are compositions comprising lopinavir alone or in combination with ritonavir for use as a medicament in the treatment of cancer or benign proliferative disorders (warts) or in the prevention of the development of cancer. Pharmaceutical compositions formulated for topical application comprising a therapeutically effective amount of lopinavir or a therapeutically effective amount lopinavir and ritonavir in a pharmaceutically acceptable vehicle are also provided. Also disclosed are methods of treating a patient having an HPV related dysplasia of the cervix comprising administering to said patient a therapeutically effective dose of the disclosed pharmaceutical compositions.

31 Claims, 16 Drawing Sheets

| Pre-treatment Diagnosis | 1 Month Post-Treatment | 3 Months Post-Treatment |
|---|---|---|
| Positive for high-risk HPV | Negative for high-risk HPV | Negative for high-risk HPV |
| Severe Dyskaryosis HSIL | Normal Cytology | Normal Cytology |

(B)

| Pre-treatment Diagnosis | 1 Month Post-Treatment | 3 Months Post-Treatment |
|---|---|---|
| Positive for high-risk HPV | Negative for high-risk HPV | Negative for high-risk HPV |
| Severe Dyskaryosis HSIL | Severe Dyskaryosis HSIL | Normal Cytology |

Fig 1 continued (C)

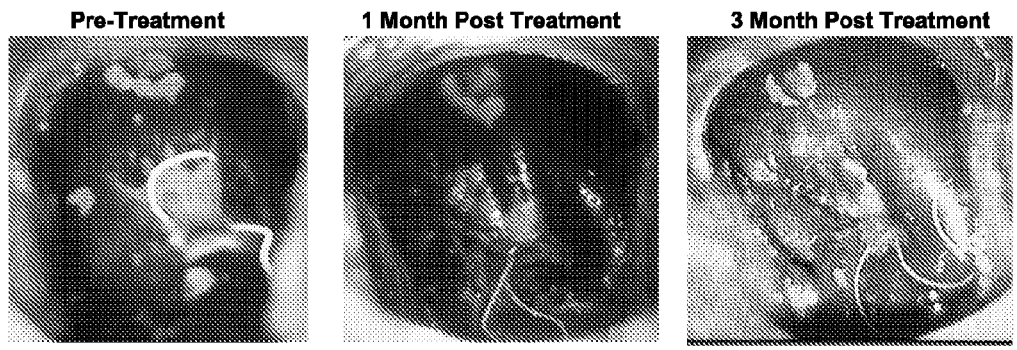

| Pre-treatment Diagnosis | 1 Month Post-Treatment | 3 Months Post-Treatment |
|---|---|---|
| Positive for high-risk HPV | Negative for high-risk HPV | Negative for high-risk HPV |
| Severe Dyskaryosis HSIL | Severe Dyskaryosis HSIL | Borderline Cytology |

(D)

| Pre-treatment Diagnosis | 1 Month Post-Treatment | 3 Months Post-Treatment |
|---|---|---|
| Positive for high-risk HPV | Negative for high-risk HPV | Negative for high-risk HPV |
| LSIL | Normal Cytology | Normal Cytology |

Abbreviations
PSC – Patient Support Centre
CCC – Comprehensive Care Clinic (HIV/AIDS)
GOPC – Gynaecology Out-Patient

FIGURE 9:
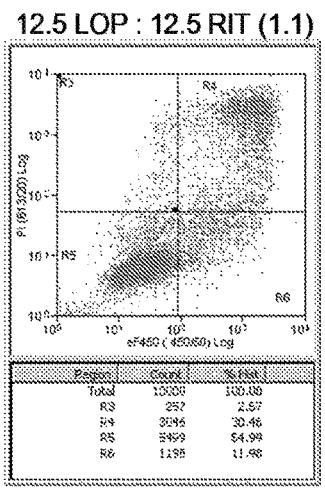
12.5 LOP : 12.5 RIT (1.1)
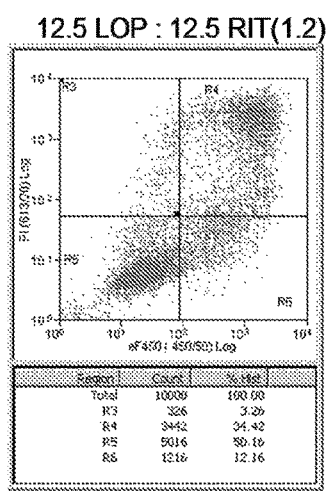
12.5 LOP : 12.5 RIT(1.2)
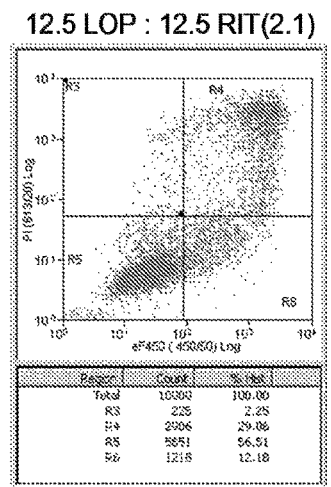
12.5 LOP : 12.5 RIT(2.1)
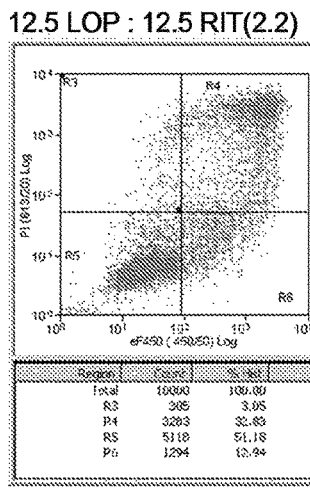
12.5 LOP : 12.5 RIT(2.2)
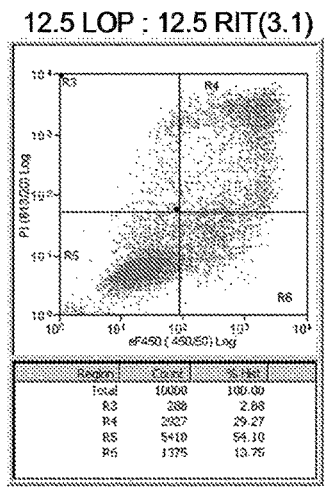
12.5 LOP : 12.5 RIT(3.1)
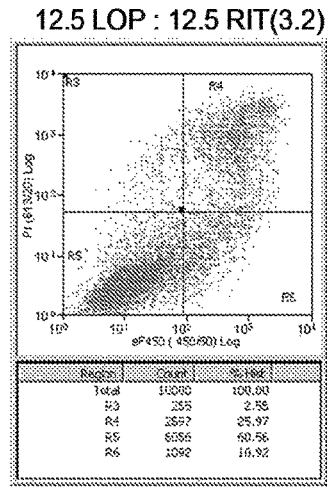
12.5 LOP : 12.5 RIT(3.2)
Intra-Sample Variance
Well 1
R4: 3.98 percentage points
R6: 0.18 percentage points
Well 2
R4: 3.77 percentage points
R6: 0.76 percentage points
Well 3
R4: 3.30 percentage points
R6: 2.83 percentage points

FIGURE 10:
20 LOP : 5 RIT (1)     20 LOP : 5 RIT (2)     20 LOP : 5 RIT (3)
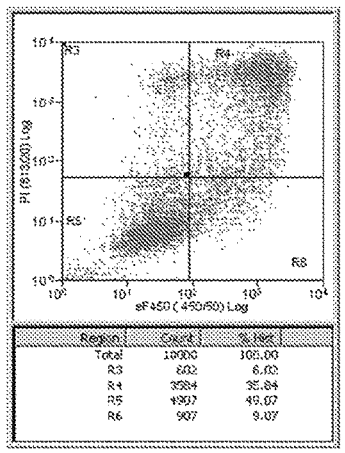 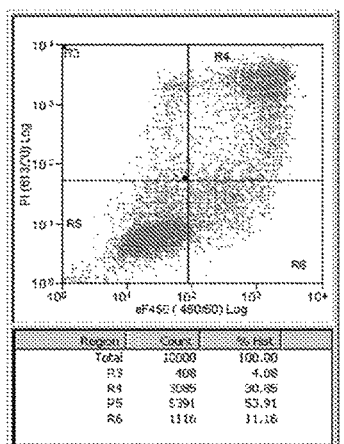 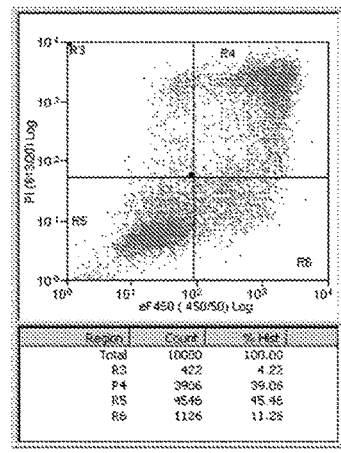
21 LOP : 4 RIT(1)     21 LOP : 4 RIT (2)     21 LOP : 4 RIT(3)
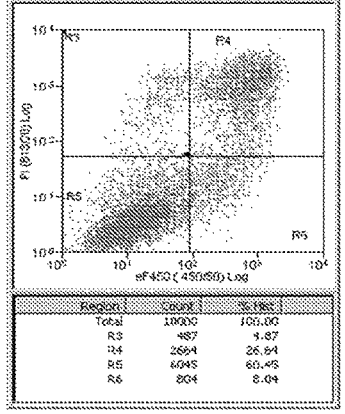 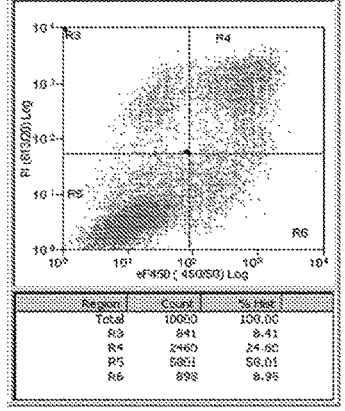 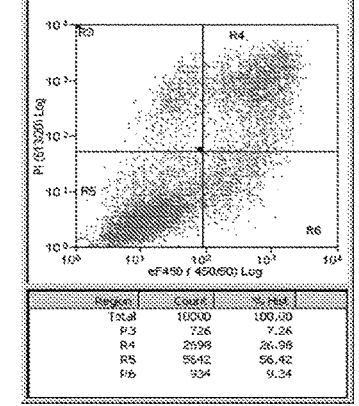
23 LOP : 2 RIT(1)     23 LOP : 2 RIT(2)     23 LOP : 2 RIT(3)
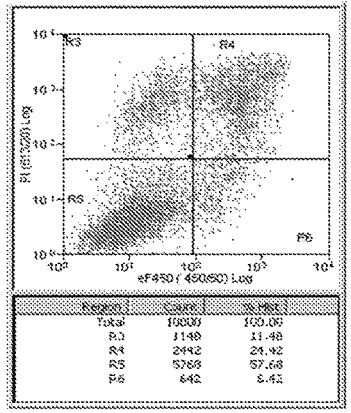 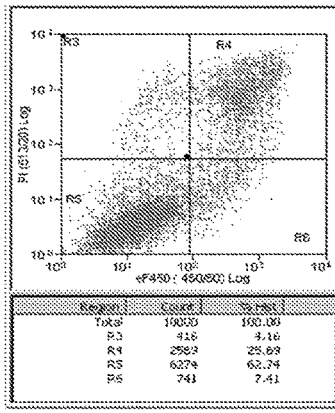 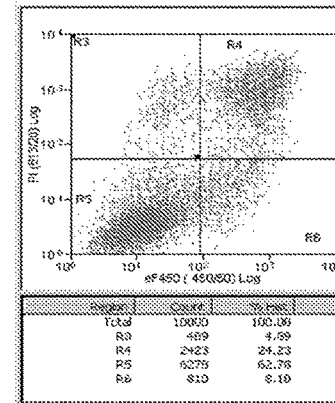

TREATMENT OF CANCER AND BENIGN PROLIFERATIVE DISORDERS

CROSS-REFERENCE TO RELATED APPLICATIONS

This application is a National Phase of International Application No. PCT/GB2014/053169 filed Oct. 23, 2014, currently pending, which designated the U.S. and that International Application was published under PCT Article 21(2) in English. Both applications also include a claim of priority under 35 U.S.C. §119(a) and §365(b) to British patent application Nos. GB 1318742.2 filed Oct. 23, 2013, now expired, and GB 1409362.9 filed May 27, 2014, now expired, the entirety of which is hereby incorporated by reference.

Provided herein are methods and compositions for treating and/or inhibiting the development or progression of cancers (particularly HPV induced cancers) and benign proliferative disorders. In particular, provided are compositions comprising lopinavir and ritonavir for use in treating and/or inhibiting the progression of HPV related dysplasia of the cervix.

BACKGROUND

Many different forms of cancer exist, and it is believed that there are many different causes of the disease. The incidence of cancer varies, but it represents the second highest cause of mortality, after heart disease, in most developed countries. Current estimates suggest that one in three Americans alive at present will suffer from some form of cancer. There is a well-recognised need to develop new and improved therapies for treating cancers. Furthermore, there is also a requirement to develop therapeutic agents that could be used to inhibit the development of cancer in the general population, susceptible high-risk individuals or as an agent to prevent re-occurrence of disease in individuals already affected.

Human tumour viruses are recognised to be a major cause of human cancer, and there is a great deal of evidence which supports the contention that these viruses cause cancer by inducing genetic instability in infected cells. Indeed, both the human T-cell leukemia virus type 1 (HTLV1) Tax and the human papilloma virus type 16 (HPV16) E6 oncoproteins are known to induce genetic instability producing abnormal numbers of centrosomes, multinucleation and nuclear atypia.

One approach to the treatment of cancers caused by viruses is disclosed in International Publication No. WO2005/053694, which outlines the use of certain HIV protease inhibitors (which had previously been proposed for use as orally ingested medicaments for the systemic clinical management of retroviral infections such as HIV) as being clinically useful for topical administration to tissues to prevent or treat malignancies caused by human papilloma virus. The authors recognised that HIV protease inhibitors, such as indinavir, were useful for treating human papilloma virus (HPV) infections and particularly cancers associated with such infections. The work was based on the author's realisation that a chymotryptic activity of the proteasome may be the preferred target for treatment of HPV infections and it is known that Indinavir and related inhibitors can suppress the chymotryptic activity of the 26S proteasome. Thus it was speculated that indinavir and related compounds act to inhibit the chymotryptic activity of the proteasome and could thereby be useful for treating HPV infections and in particular HPV infections that lead to the development of cancer (e.g. in the cervix, mouth, anus, vagina and penis).

International Publication No. WO2005/053694 went on to contemplate that a number of HIV protease inhibitors could be used in the treatment of cancer (indinavir was identified as the most preferred) but also highlighted that certain HIV protease inhibitors (particularly ritonavir) did not appear to have the same activity as inhibitors such as indinavir. Indeed combinations of ritonavir and other protease inhibitors were actually shown to be less effective in this regard and therefore ritonavir fell outside the definition of the efficacious inhibitors contemplated in that specification.

A number of clinical trials for cancer have been conducted using ritonavir alone or ritonavir with lopinavir. However, each of these trials suggested the compounds would not be useful in the field of oncology. For instance, ritonavir has shown activity against pre-invasive cells derived from the cervix but was not effective against more advanced invasive cervical disease (Barillari, G., Iovane, A., Bacigalupo, I., Palladino, C., Bellino, S., Leone, P., Monini, P., Ensoli, B., Ritonavir or saquinavir impairs the invasion of cervical intraepithelial neoplasia cells via a reduction of MMP expression and activity. *AIDS*, 2012, 26(8):909-19.). This finding would potentially lead a skilled person to discount using ritonavir since elimination of early stage neoplastic cells (without being effective against advanced cells) could promote the evolution of more invasive forms of the disease. Another clinical trial with ritonavir (Laurent, N., de Boüard, S., Guillamo, J. S., Christov, C., Zini, R., Jouault, H., Andre, P., Lotteau, V., Peschanski, M. Effects of the proteasome inhibitor ritonavir on glioma growth in vitro and in vivo. *Mol Cancer Ther.* 2004, 3(2):129-36) reported that ritonavir alone against glioma had no effect in vivo. A subsequent trial of ritonavir/lopinavir in humans had very little effect against glioma (Ahluwalia, M. S., Patton, C., Stevens, G., Tekautz, T., Angelov, L., Vogelbaum, M. A., Weil, R. J., Chao, S., Elson, P., Suh, J. H., Barnett, G. H., Peereboom, D. M., Phase II trial of ritonavir/lopinavir in patients with progressive or recurrent high-grade gliomas. *J. Neurooncol.* 2011, 102(2):317-21)

Infection with high-risk types of HPV has now been established as the main aetiological agent for invasive cervical cancer (ICC) and globally there are >270,000 deaths from this disease per annum with over 85% of these occurring in low resource countries. For example, in Kenya it is the most common cancer accounting for between 18-23% of all diagnosed cases of cancer.

The development of ICC can take 10-20 years and is preceded by HPV related pre-invasive pathology which is characterised as either low-grade (CIN1) or high-grade cervical intraepithelial neoplasia (CIN2/3). Lesions can be screened for by cervical cytology testing where they are diagnosed (or graded) as either borderline atypical squamous cells of undetermined significance (ASCUS), low-grade squamous intraepithelial lesions (LSIL) or high-grade squamous intraepithelial lesions (HSIL).

The reduction in ICC related mortality in the developed world has been largely dependent on organised cytology screening and similar trends in cervical cancer mortality have been achieved by organised single screen and treatment in the third world. However, in the poorer nations lack of resources and health education means that most pre-invasive cervical disease remains undiagnosed and untreated. Thus, where resources are limited, low-cost screening and treatment options are clearly a high priority.

Current treatment options in clinical practice are either by ablative (destructive) or excisional modalities. Systematic reviews have demonstrated that these treatment modalities have similar success rates but have different morbidities. In the developed world, Large Loop Excision of the Transformation Zone LLETZ (aka loop electrosurgical excision procedure—LEEP) is used in the majority of colposcopy clinics. Over 80% of these procedures are performed under local analgesia and the whole of the transformation zone is available for subsequent histological examination. The procedure is associated with a risk of primary/secondary haemorrhage, prolonged discharge, infection and a risk of preterm delivery in subsequent pregnancies. The former side effects can be problematic particularly in low resource countries. Ablative treatment in the form of cold coagulation and cryotherapy are often advocated for use in these settings since these are low cost, require minimal infrastructure and can be carried out by trained non-medical health professionals. However, some studies have suggested that cryotherapy has a higher failure rate compared to other treatment modalities.

There are a variety of locally-applied, non-surgical approaches which have been evaluated for the treatment of cervical dysplasia including; photodynamic therapy (PDT); off-licence use of the anti cytomegalovirus (CMV) drug cidofovir; local application of the immune activator Imiquimod and direct application of the cytotoxic drug 5 flurouracil (5FU). Although some of these alternative treatment modalities show promise, their treatment outcomes are inferior to the reported 80-95% success rates obtained in quality assured colposcopy units.

An effective, inexpensive, non-surgical, self-applied treatment for HPV related cervical dysplasia would have great potential particularly in low resource settings. Furthermore, improved compliance with topical treatment would be enhanced, if the side effects are minimised.

SUMMARY

Disclosed herein are compositions comprising lopinavir alone or in combination with ritonavir for use as a medicament in the treatment of cancer or benign proliferative disorders (warts) or in the prevention of the development of cancer.

Pharmaceutical compositions formulated for topical application comprising a therapeutically effective amount of lopinavir or a therapeutically effective amount lopinavir and ritonavir in a pharmaceutically acceptable vehicle are also provided.

Also disclosed are methods of treating a patient having an HPV related dysplasia of the cervix comprising administering to said patient a therapeutically effective dose of the disclosed pharmaceutical compositions.

BRIEF DESCRIPTION OF THE DRAWINGS

The summary, as well as the following detailed description, is further understood when read in conjunction with the appended drawings. For the purpose of illustrating the disclosed compositions and methods, there are shown in the drawings exemplary embodiments of the compositions and methods; however, the compositions and methods are not limited to the specific embodiments disclosed. In the drawings:

FIG. 1, comprising FIGS. 1A-1D, illustrate: A) regression of a HSIL lesion stained with Lugol's iodine 1 & 3 months post-treatment—the patient became HPV negative; B) regression of a HSIL lesion stained with Lugol's iodine at 1 & 3 months post-treatment—the patient became HPV negative at 1 month and cytologically normal at 3 months; C) regression of a HSIL lesion stained with Lugol's iodine at 1 & 3 months post treatment—the patient was HPV negative at 1 & 3 months and had borderline cytology at 3 months; and D) an LSIL lesion stained with Lugol's iodine, which showed clearance of HPV and normal cytology at 1 and 3 months post-treatment.

FIGS. 3A-3C, illustrates the combined results of Cervista® HPV test, cytology and PCR HPV genotype analysis for women initially diagnosed with HSIL in Example 2. The Cervista HPV titre is indicated by the height of the bar graph above the cut off and the cytology status is indicated by colour and shading with the HPV type shown above the bar. (A) Represents the results before treatment with lopinavir; (B) Represents results after 4 and (C) 12 weeks after treatment.

FIGS. 4A-4C, illustrates the combined results of the Cervista® HPV test, cytology and PCR HPV genotype analysis for women initially diagnosed with ASCUS/LSIL in Example 2. The Cervista HPV titre is indicated by the height of the bar graph above the cut off and the cytology status is indicated by colour and shading with the HPV type shown above the bar. (A) Represents the results before treatment with lopinavir; (B) Represents results after 4 and (C) 12 weeks after treatment.

FIG. 7, comprising

FIG. 9, illustrates scatter plot analysis of triplicate cultures treated with 1:1 (12.5 µM lopinavir+12.5 µM ritonavir) with an additional analysis of one culture repeated 3 times to determine the intra cytometer assay variance. (Note: Cells in the R6 quadrant are in earlier stages of apoptosis).

FIG. 10, illustrates scatter plot analysis of triplicate cultures treated with 4:1 (20 µM lopinavir+5 µM ritonavir) plus cultures treated with decreasing amounts of ritonavir (21 µM lopinavir+4 µM ritonavir and 23 µM lopinavir+2 µM ritonavir).

DETAILED DESCRIPTION OF ILLUSTRATIVE EMBODIMENTS

Figure 2:
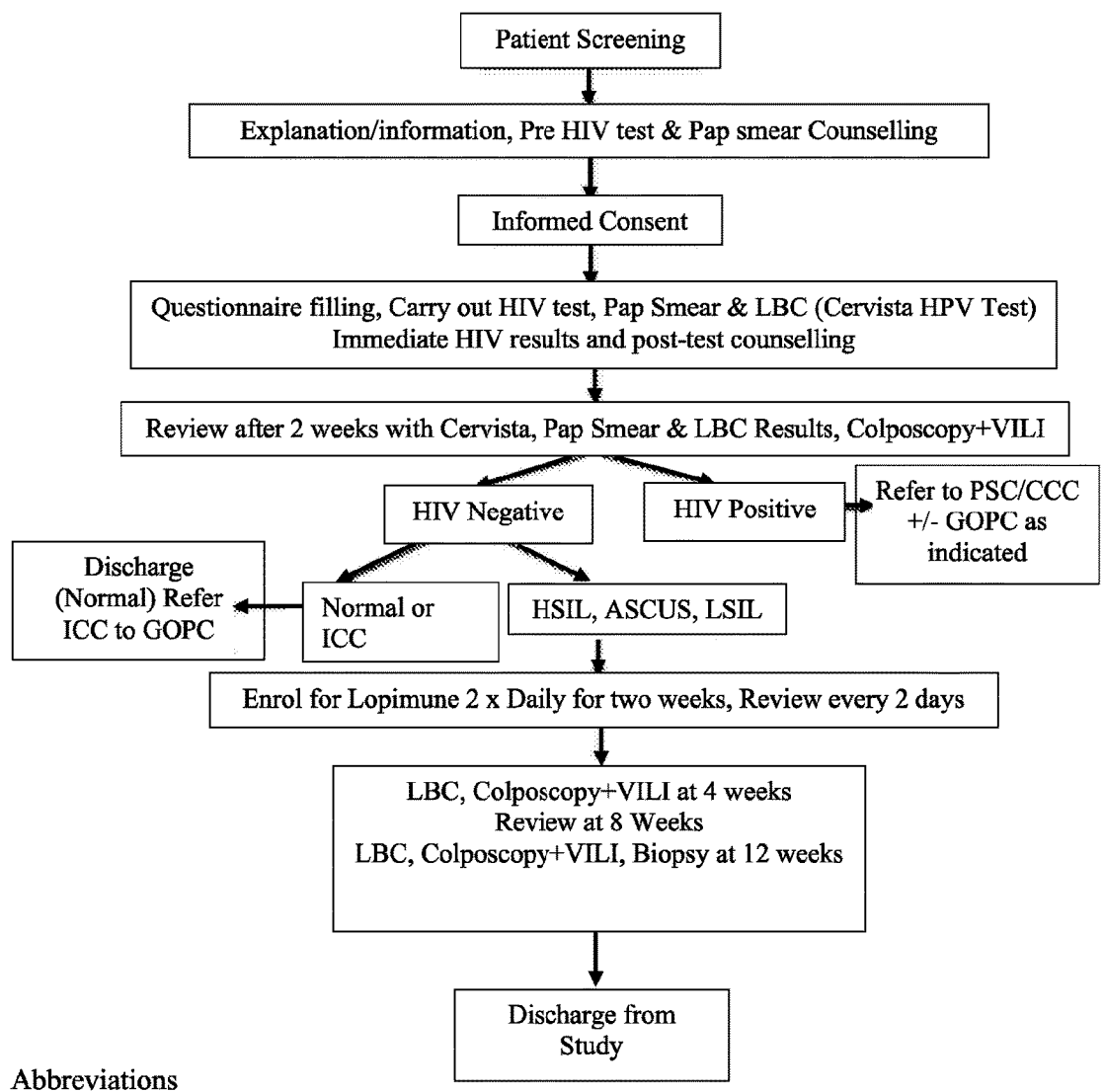
FIG. 2, illustrates an exemplary patient screening, testing and management flow chart used for the study described in Example 2.

The disclosed compositions and methods may be understood more readily by reference to the following detailed description taken in connection with the accompanying figures, which form a part of this disclosure. It is to be understood that the disclosed compositions and methods are not limited to the specific compositions and methods described and/or shown herein, and that the terminology used herein is for the purpose of describing particular embodiments by way of example only and is not intended to be limiting of the claimed compositions and methods.

Reference to a particular numerical value includes at least that particular value, unless the context clearly dictates otherwise. When a range of values is expressed, another embodiment includes from the one particular value and/or to the other particular value. Further, reference to values stated in ranges include each and every value within that range. All ranges are inclusive and combinable.

When values are expressed as approximations, by use of the antecedent "about," it will be understood that the particular value forms another embodiment.

It is to be appreciated that certain features of the disclosed compositions and methods which are, for clarity, described herein in the context of separate embodiments, may also be provided in combination in a single embodiment. Conversely, various features of the disclosed compositions and methods that are, for brevity, described in the context of a single embodiment, may also be provided separately or in any subcombination.

As used herein, the singular forms "a," "an," and "the" include the plural.

The following abbreviations are used herein: human papilloma virus (HPV); Atypical squamous cells of undetermined significance (ASC-US); Low grade squamous intraepithelial lesion (LSIL); Atypical squemous cells—cannot exclude HSIL (ASC-H); High grade squamous intraepithelial lesion (HSIL); Squamous cell carcinoma (SCC); Abnormal glandular cells (AGC); Cervical intraepithelial neoplasia 1 (CIN1); Cervical Intraepithelial neoplasia 2 (CIN2); Cervical intraepithelial neoplasia 3 (CIN3); Carcinoma in situ (CIS); Invasive Cervical Carcinoma (ICC).

The term "about" when used in reference to numerical ranges, cutoffs, or specific values is used to indicate that the recited values may vary by up to as much as 10% from the listed value. As many of the numerical values used herein are experimentally determined, it should be understood by those skilled in the art that such determinations can, and often times will, vary among different experiments. The values used herein should not be considered unduly limiting by virtue of this inherent variation. Thus, the term "about" is used to encompass variations of ±10% or less, variations of ±5% or less, variations of ±1% or less, variations of ±0.5% or less, or variations of ±0.1% or less from the specified value.

As used herein, "treating" and like terms refer to reducing the severity and/or frequency of HPV induced symptoms, eliminating HPV induced symptoms and/or the underlying cause of said symptoms, reducing the frequency or likelihood of HPV induced symptoms and/or their underlying cause, delaying, preventing and/or slowing the progression of HPV induced cancers or benign proliferative disorders, and improving or remediating damage caused, directly or indirectly, by HPV infections. As used herein, the phrase "therapeutically effective dose" refers to an amount of a composition comprising lopinavir, or more preferably lopinavir and ritonavir, as described herein, effective to achieve a particular biological or therapeutic result such as, but not limited to, biological or therapeutic results disclosed, described, or exemplified herein. The therapeutically effective dose may vary according to factors such as the disease state, age, sex, and weight of the individual, and the ability of the composition to cause a desired response in a subject. Such results include, but are not limited to, the reduction, remission, and/or regression of the malignant disease or prevention of the development of malignant disease, as determined by any means suitable in the art.

As used here, "subject" includes a vertebrate, mammal, domestic animal or preferably a human being.

The "pharmaceutically acceptable vehicle" may be any physiological vehicle known to those of ordinary skill in the art useful in formulating pharmaceutical compositions.

As used herein, "ovule" refers to a cream or gel containing solid or semi-solid suppository configured for insertion into the vagina.

Disclosed herein are compositions comprising lopinavir and ritonavir for use as a medicament in the treatment of cancer or benign proliferative disorders (warts) or in the prevention of the development of cancer. Contrary to what was known in the prior art, the inventors have found that while ritonavir was previously thought to have little or known efficacy in treating HPV-related conditions (see, e.g., WO2005/053694), lopinavir and ritonavir act synergistically to treat and inhibit progression of such conditions, with the combination of active agents producing unexpectedly superior results over the use of either active agent alone.

The compositions according to the first aspect of the invention are useful in the treatment of cancer and particularly useful for preventing the development of cancers. Accordingly, normal subjects (i.e. subjects with no detectable cancer), subjects with pre-malignant cells or particularly cancer prone subjects may be treated according to the invention (preferably by topical administration of the inhibitors) with a view to preventing the development of cancer.

The invention, to the extent that it is applicable to the prevention and treatment of cancer, may be applied to a wide range of cancers such as ovarian carcinoma, breast carcinoma, lung carcinoma, uterine carcinoma, cervical carcinoma and thyroid carcinoma. It is also applicable to cancer prone conditions. The invention is applicable particularly, but by no means exclusively, to pre-cancerous conditions and cancers caused by oncogenic viruses, e.g. high-risk or even low-risk forms of human papilloma viruses (HPVs).

According to a preferred embodiment of the invention, the compositions may be administered to treat, and particularly prevent, the development of cervical cancer. It is most preferred that the inhibitors are used to treat, or prevent the development of cervical cancers caused by HPV (particularly high-risk types of HPV such as HPV16). The surprising efficacy of compositions used according to the first aspect of the invention against HPV related HSIL/CIN in humans could thus not be predicted from any of the in vitro, in vivo or clinical trial studies carried out to date.

In the developed nations that have cervical screening programs, HPV testing and cervical cytology are currently in a state of flux. At present, the cervical smear (or Pap test) is usually carried our prior to HPV testing with follow on procedures depending on the results obtained. However, depending on geographical location the HPV test may be given first. Table 1 shows a typical recommended management protocol based on the combined results of HPV and Pap tests.

TABLE 1

Recommended Management of combined HPV and Pap tests

| HPV test | Pap test | Management |
|---|---|---|
| Negative | Negative | Repeat testing in 5 years |
| Any | Negative | Repeat testing in 3 years |
| Negative | ASC-US | Repeat testing in 3 years |
| Negative | LSIL | Repeat testing in 6-12 months |
| Not performed | ASC-US | Repeat testing in 6-12 months |
| Positive | Negative | Repeat testing in 6-12 months |
| Not performed | LSIL | Immediate colposcopy |
| Positive | LSIL | Immediate colposcopy |
| Any | ASC-H | Immediate colposcopy |
| Positive | ASC-US | Immediate colposcopy |
| Any | HSIL | Immediate colposcopy |
| Any | SCC | Immediate colposcopy |
| Any | AGC | Immediate colposcopy |

Table 1 Acronyms:
Atypical squamous cells of undetermined significance (ASC-US);
Low grade squamous intraepithelial lesion (LSIL);
Atypical squemous cells - cannot exclude HSIL (ASC-H);
High grade squamous intraepithelial lesion (HSIL);
Squamous cell carcinoma (SCC);
Abnormal glandular cells (AGC).
Taken from Schiffman, M., Solomon, D., Clinical practice. Cervical-cancer screening with human papillomavirus and cytologic cotesting. N Engl J Med. 2013, 369(24): 2324-31

Pathology results obtained from biopsies taken at colposcopy are described as: Cervical intraepithelial neoplasia 1 (CIN1); Cervical Intraepithelial neoplasia 2 (CIN2); Cervical intraepithelial neoplasia 3 (CIN3); Carcinoma in situ (CIS); Invasive Cervical Carcinoma (ICC). HPV negative CIN1 is clinically equivalent to LSIL and is currently a rescreen in 6-12 months (watch and wait).

This recommended management protocol represents the current best clinical practice for testing women aged >25. It can be seen that immediate colposcopy is recommended for any women with LSIL cytology or greater (HSIL, etc.) in the absence of a HPV test. Women with LSIL who are shown to be HPV negative, are rescreened in 6-12 months.

A preferred window of opportunity for use of compositions according to the first aspect of the invention is between the time of initial diagnosis with HPV positive disease (ASC-US, LSIL, ASC-H, HSIL) until colposcopy, which usually takes approximately 2 weeks or longer, depending on waiting times. Based on what is observed at colposcopy, the decision is then made to either treat with surgery at this visit (See and Treat) or take biopsies for pathology which necessitates a further colposcopy visit approximately one month later. Clearly, if the colposcopy visits are timed appropriately, it may advantageously be that treatment according to the invention removes the need for surgery.

It is preferred that the compositions are formulated in a medicament that is suitable for topical application. In a most preferred embodiment, the medicament is formulated such that it is suitable for topical delivery of the active ingredients to the cervix (e.g. as a gel, cream, soft capsule, or pessary) for preventing the development of, or treating cervical cancer (e.g. caused by high-risk types of HPV such as HPV16).

Lopinavir (CAS#192725-17-0) is a protease inhibitor chemically designated as [1S-[1R*(R*), 3R*, 4R1]-N-[4-[(2,6-dimethylphenoxy0acetyl]amino]-3-hydroxy-5-phenyl-1-(phenylmethyl)pentyl]tetrahydro-alpha-(1-methylethyl)-2-oxo-1(2H)-pyrimidineacetamide. It has the molecular formula $C_{37}H_{48}N_4O_5$ and a molecular weight of 628.80.

Ritonavir (CAS#155214-67-5) is a protease inhibitor chemically designated as 10-Hydroxy-2-methyl-5-(1-methylethl)-1-[2-(1-methylethyl)-4-thiazolyl]-3,6-dioxo-8,11bis(phenylmethyl)-2,4,7,12-tetraazatridecan-13-oic acid, 5-thiazolylmethylester, [5S-(5R*,8R*,10R8,11R*)]. It has the molecular formula $C_{37}H_{48}N_6O_5S_2$ and a molecular weight of 720.95.

Pharmaceutical products are known that combine lopinavir and ritonavir. For instance LOPIMUNE is marketed by Cipla. Another example is KALETRA® which is marketed by Abbott/Abbvie for the treatment of HIV infections. Other products are manufactured by Emcure, Ranbaxy, Hetero and Matrix.

By way of example, KALETRA® is used orally and is available for oral consumption as a solution comprising 80 mg lopinavir and 20 mg ritonavir per milliliter or as a soft capsule for oral administration that comprises 133.3 mg lopinavir and 33.3 mg ritonavir.

Unexpectedly, it has been found that soft capsule versions of pharmaceutical products comprising lopinavir and ritonavir (e.g. LOPIMUNE or KALETRA®) can be administered topically (e.g. inserted into the vagina for treatment of the cervix) for the prevention or treatment of cancerous conditions or for the prevention or treatment of oncogenic viral infections. Accordingly, the soft capsule formulation of KALETRA® is an example of a formulation that may be used for topical application according to the invention, although hard tablet forms of the drug exist which may also be useful for direct topical application.

KALETRA® soft capsules comprise oleic acid, propylene glycol, PEG 35 castor oil, purified water, gelatin, sorbitol, special polyol, titanium dioxide, sunset Yellow FCF CI15985, medium chain trigylcerides, lecithin and a black printing ink (e.g. Opacode WBNSP-78-17734 black with ARTG No. 3791). It will be appreciated that these ingredients may be varied.

However, KALETRA® soft capsules are formulated for oral ingestion and in preferred embodiments it is preferred that lopinavir and ritonavir are formulated to suit the way in which they will be topically administered as discussed in more detail below. For instance, in preferred formulations for topical application to the cervix, the composition does not include pigments, dyes, or inks. In exemplary embodiments, the formulations for topical application to the cervix do not include titanium dioxide, Yellow FCF CI15985 or a black printing ink.

Preferred compositions for use according to the invention are vaginal suppositories and ovules that comprise lopinavir and ritonavir which at least preclude the use of KALETRA® soft capsules. Such vaginal suppositories, or ovules, may be between about 2 and 8 grams. Such vaginal suppositories, or ovules, typically may use polyethylene glycol as a main carrier for the inhibitors. The balance of the carrier may be made up of Oleic acid, PEG 35, castor oil, purified water, gelatin and sorbitol special polyol etc. Lopinavir and Ritonavir are virtually insoluble in water and it is preferred that such organic bases (or equivalents thereof) are formulated in such vaginal suppositories.

The disclosed compositions are not only useful for treating actual cancers but are also surprisingly useful for preventing the development of cancer, particularly in patients that may exhibit any of the previously described pre-cancerous lesions in HPV-positive patients. Accordingly, compositions comprising lopinavir and ritonavir may be advantageously used as a prophylactic.

The compositions may be given to subjects with a genetic disposition to developing cancer (most particularly cervical carcinoma) or even those facing environmental risk (e.g. people exposed to carcinogens). In a preferred embodiment, the compositions may be given to women who are at risk of developing cancer. Such women can include those who have been diagnosed as having a high risk HPV infection of the urino-genital tract (and particularly the cervix). At the time of diagnosis, there may not be any clinical evidence that such women have a cervical carcinoma or even precancerous cells of the cervix, yet women with such infections are believed to be at risk of developing cervical cancer. The compositions may be topically applied to the cervix of women with a viral infection of the cervix with a view to treating the viral infection and thereby preventing the development of cancer at a future date.

The compositions may be used to prevent or treat cancer as a monotherapy (i.e. use of the two inhibitors alone) or in combination with other compounds or treatments used in cancer therapy (e.g. chemotherapeutic agents, radiotherapy).

It is most preferred that the compositions are used to treat humans (e.g. women with or at risk of developing cervical cancer). However, it will be appreciated that the compositions may also have some veterinary use.

The medicaments used according to the invention may take a number of different forms depending, in particular, on the manner in which the medicament is to be applied topically. Thus, for example, the medicament may be in the form of a powder, tablet, capsule, liquid, ointment, cream, gel, hydrogel, ovule, suppository, aerosol, spray, micelle, liposome or any other suitable form that may be administered to a person or animal. It will be appreciated that the vehicle of the medicament of the invention should be one which is well tolerated by the subject to whom it is given and enables delivery of the inhibitors to the effected or target site.

In some aspects, the compositions can be formulated for topical use (e.g. as gels, creams or ointments). For instance, when used to treat (or prevent the development of) cervical cancer, the compositions can be formulated as gels, creams or ointments that may be applied directly to the cervix by techniques known to the art. Alternatively, the compositions may be formulated as a vaginal suppository (or incorporated within a pessary) according to techniques known to the art.

In other aspects, the medicaments may be in the form of an ovule. The ovule can comprise a cream or gel located within a coating, the coating configured to melt and release the cream or gel upon being administered intravaginally. Alternatively, the ovule can consist of a cream or gel that is configured to melt upon being administered intravaginally. The compositions may also be formulated as a soft capsule wherein the outer layer of the capsule suitably dissolves at the site of application to allow the release of the compositions. For instance, unexpectedly, it has been established that KALETRA® (or similar) soft capsules may be administered to the cervix of a woman in need of treatment. Accordingly, such capsules are effective for topical delivery of therapeutically effective amounts of lopinavir and ritonavir to the cervix when inserted into the vagina of a subject. However, as mentioned previously, preferred embodiments of the invention exclude the use of lopinavir/ritonavir compositions such as KALETRA® (or similar) that have actually been formulated for oral administration and preferred embodiments include lopinavir/ritonavir compositions formulated for topical administration (e.g. to the cervix).

It will be appreciated that the amount of lopinavir and ritonavir required is determined by biological activity and bioavailability, which in turn depends, in part, on the precise mode of administration, the physicochemical properties of the composition employed, and whether the compositions are being used as a monotherapy or in a combined therapy with other oral or topical anti-cancer or anti HIV agents. Indeed it is also possible that topical lopinavir/ritonavir could be applied in addition to oral dosing of the same compounds or other anti HIV protease inhibitors. The frequency of administration will also be influenced by the abovementioned factors and particularly the half-life of the compound within the subject being treated.

Daily doses may be given as a single administration (e.g. as a soft capsule, vaginal suppository, ovule or pessary). Alternatively, administration may be twice or more times during a day. As an example, the compositions (for preventing the development of cervical cancer) may be topically administered twice a day.

Optimal dosages to be administered may be determined by those skilled in the art, and will vary with the strength of the preparation, the mode of administration, and the advancement of the disease condition. Additional factors depending on the particular subject being treated will result in a need to adjust dosages, including, for example, subject age, weight, gender, diet, and time of administration.

Suitable amounts of lopinavir in the disclosed compositions include from about 0.1 mg to about 2.0 g. In some embodiments, the amount of lopinavir in the composition can be from about 10 mg to about 1.5 g. In some embodiments, the amount of lopinavir in the composition can be from about 100 mg to about 1.0 g. In some embodiments, the amount of lopinavir in the composition can be from about 150 mg to about 900 mg. In some embodiments, the amount of lopinavir in the composition can be from about 250 mg to about 800 mg. In some embodiments, the amount of lopinavir in the composition can be from about 350 mg to about 700 mg. In some embodiments, the amount of lopinavir in the composition can be from about 500 mg to about 600 mg.

Suitable amount of ritonavir in the disclosed compositions include from about 0.1 mg to about 500 mg. In some embodiments, the amount of ritonavir in the composition can be from about 10 mg to about 400 mg. In some embodiments, the amount of ritonavir in the composition can be from about 20 mg to about 300 mg. In some embodiments, the amount of ritonavir in the composition can be from about 30 mg to about 200 mg. In some embodiments, the amount of ritonavir in the composition can be from about 50 mg to about 100 mg.

For a human adult, between about 0.1 mg and about 2.0 g of lopinavir, and about 0.1 mg and about 500 mg of ritonavir can be preferably topically administered to the target tissue per day. Preferably between about 10 mg and about 1.0 g of lopinavir and about 5 mg and about 200 mg of ritonavir can be topically administered to the target tissue per day. More preferably between about 100 mg and about 600 mg of lopinavir and between about 30 mg and about 175 mg of ritonavir can be topically administered to the target tissue per day.

In one embodiment, about 266.6 mg of lopinavir and about 66.6 mg ritonavir per day may be administered to the cervix of a woman. This may be achieved by inserting, twice a day, a soft gel capsule of Lopimune containing 133.3 mg of lopinavir and 33.3 mg of ritonavir in the vagina of the woman being treated.

In another embodiment, about 533 mg of lopinavir and about 126 mg ritonavir per day may be administered to treat the cervix of a woman. This may be achieved by inserting, twice a day, two soft gel capsules of Lopimune containing 133.3 mg of lopinavir and 33.3 mg of ritonavir in the vagina of the woman being treated.

In a further embodiment, between about 400 mg to about 600 mg of lopinavir and about 100 mg to about 150 mg ritonavir per day may be administered to treat the cervix of a woman. This may be administered as a single vaginal suppository, or ovule, once a day (preferably last thing at night) and should ideally be applied for between 2-4 weeks.

The ratio of lopinavir to ritonavir in the medicament may be varied. Suitable ratios of lopinavir to ritonavir in the composition include, for example, from about 1:10 to about 10:1. In some embodiments, the ratio of lopinavir to ritonavir in the composition is about 1:1. In some embodiments, the ratio of lopinavir to ritonavir in the composition is about 2:1. In some embodiments, the ratio of lopinavir to ritonavir in the composition is about 3:1. In some embodiments, the ratio of lopinavir to ritonavir in the composition is about 4:1. In some embodiments, the ratio of lopinavir to ritonavir in the composition is about 5:1. In some embodiments, the ratio of lopinavir to ritonavir in the composition is about 10:1. In some embodiments, the ratio of lopinavir to ritonavir in the composition is from about 1:1 to about 4.1. In other embodiments, the ratio of lopinavir to ritonavir in the composition is from about 1:1 to less than 4:1. In some aspects, it is preferred that the ratio of lopinavir to ritonavir is about 4:1. In other aspects, it is preferred that the ratio of lopinavir to ritonavir is less than 4:1. Preferably, the ratio of lopinavir:ritonavir is one which exhibits synergistic efficacy above and beyond that which would have been expected from the use of either active agent alone.

The medicament may be administered to a subject for as long as treatment is required. The length of time for which treatment will be required will depend upon the exact condition being treated or prevented and its severity. A skilled person will appreciate that treatment should be maintained in view of a number of factors which will include any requirement to eradicate any oncogenic virus (e.g. HPV); to reduce or eradicate cells with a precancerous or cancerous phenotype; or to shrink or eradicate any tumour. Typically a course of treatment should be for 2-4 weeks, 7-21 days or for about 14 days. After this time a clinician may assess whether the course of treatment has been successful. A decision may then be made whether or not to continue treatment.

It will be appreciated that a clinician may wish to take into account menstruation when deciding on a treatment regimen for conditions relating to the cervix. Accordingly, a preferred treatment regimen may be for about 14-21 days and can be administered between menses. A clinician may elect to stop topical treatment of the cervix during menses and recommence a new course of treatment in the next menstrual cycle. By way of example, a preferred treatment regimen can be: (1) 14-21 days of administration; (2) followed by 1-14 days without treatment (during which menses may occur if treating the cervix); and (3) a further cycle of 14-21 days of treatment if this is considered medically necessary. In a most preferred embodiment, the cervix of a women may be treated such that she receives about 266.6 mg of lopinavir and about 66.6 mg ritonavir per day for 14-21 days; treatment can then be stopped for 1-14 days and a clinical reassessment can be conducted; then, if necessary a second treatment cycle of about 533 mg of lopinavir and about 126 mg ritonavir per day can be administered for a further 14-21 days. After the second cycle a further clinical assessment can be made and a decision made about whether or not subsequent treatment cycles are required.

Unexpectedly, one treatment cycle of 14 days is very effective for eradicating oncogenic viral infection and reducing or eradicating precancerous or cancerous lesions (see the Examples).

By way of further example, and without intending to be limiting, a preferred treatment regimen for treating the cervix of a woman in need of treatment can be: (1) 14-21 days of administration; (2) optionally followed by 1-14 days without treatment (during which menses may occur); and (3) a further cycle of 14-21 days of treatment if this is considered medically necessary. The women may be treated such that she receives between about 400 mg and about 600 mg of lopinavir and between about 100 mg and about 150 mg ritonavir per day as a single dose which is ideally self-administered last thing at night (i.e. just before retiring for sleep).

Also disclosed herein are pharmaceutical compositions for topical application comprising a therapeutically effective amount of lopinavir and ritonavir and a pharmaceutically acceptable vehicle.

In one embodiment, the pharmaceutically acceptable vehicle can be a liquid and the composition can be a solution. In another embodiment, the vehicle can be a gel and the composition can be a suppository or pessary. In a further embodiment, the vehicle can be an emulsion (or other pharmaceutically acceptable base) and the composition can be a cream.

Liquid vehicles are used in preparing solutions, suspensions, emulsions, syrups, elixirs and pressurized compositions. The active ingredient can be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilizers, emulsifiers, buffers, preservatives, suspending agents, thickening agents, colors, viscosity regulators, stabilizers or osmo-regulators. Suitable examples of liquid vehicles include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). The vehicle can also be an oily ester such as ethyl oleate and isopropyl myristate. The liquid vehicle for pressurized compositions can be halogenated hydrocarbon or other pharmaceutically acceptable propellent.

It is preferred that the pharmaceutical composition is a vaginal suppository. Conventional vehicles, coatings and other constituents of vaginal suppositories may be chosen by one skilled in the art to form a suppository that is characterised by the fact it comprises therapeutically effective amounts of lopinavir and ritonavir.

Preferred vaginal suppositories typically may use polyethylene glycol as a main vehicle for lopinavir and ritonavir. The balance of the vehicle may be made up of, for example, Oleic acid, PEG 35, castor oil, purified water, gelatin, sorbitol special polyol, or any combination thereof. Lopinavir and ritonavir are virtually insoluble in water and it is preferred that such organic bases (or equivalents thereof) are formulated in such vaginal suppositories.

Previously published in vitro work on the potential activity of lopinavir (alone) against HPV positive cervical cancer cell lines suggested that lopinavir might have some activity against this cell type (Int'l Publ. No. WO2005/053694). However, most compounds which show potential anticancer activity from in vitro studies usually fail to show activity either in vivo or in clinical trials in humans. For example, "[d]espite their importance for drug testing, in vitro methods are beset by pitfalls and inherent limitations" (Zips et al. (2005: In Vivo January-February 19(1) p 1-7). Indeed since formal screening began in 1955, many thousands of drugs have shown activity in either cell culture based or animal models, but only 39 that are used exclusively for chemotherapy, as opposed to supportive care, have won approval from the U.S. Food and Drug Administration. "The fundamental problem in drug discovery for cancer is that model systems are not predictive at all" (Alan Oliff (Executive Director, Merck Research Laboratories, West Point, Pa.).

The typical cancer drug testing scheme is to proceed with a variety of in vitro methods which, if successful, subsequently leads to testing in a variety of experimental in vivo models prior to any clinical studies in humans (See Zips et al. supra). The failure rate of compounds as they move through this testing cascade is very high. Thus, since only limited in vitro studies were carried out on the activity of lopinavir (alone) against HPV positive cervical cancer cell lines, the results of the clinical trial of the compositions according to the first aspect of the invention against HPV related cervical neoplasia in humans (See Examples 1 & 2) are entirely novel, unexpected and remarkable. Furthermore, the efficacy of lopinavir alone can also be considered to be unexpected, and according to a further aspect of the invention, there is provided a composition comprising lopinavir for use as a medicament in the treatment of cancer or benign proliferative disorders (warts) or in the prevention of the development of cancer. Accordingly, lopinavir may be used as contemplated above but without the inclusion of ritonavir.

Preferably, the pharmaceutical composition comprises a synergistic amount of lopinavir and ritonavir. In some embodiments, for example, the synergistic amount of lopinavir and ritonavir can be from about 1:1 to about 4:1 lopinavir to ritonavir. In other embodiments, the synergistic amount of lopinavir to ritonavir can be from about 1:1 to less than 4:1 lopinavir to ritonavir.

The disclosed pharmaceutical compositions can be formulated for intravaginal delivery. Suitable formulations for intravaginal delivery include, but are not limited to, a gel, cream, ointment, lotion, ovule, soft capsule, suppository, pessary, or any combination thereof. In some aspects, the pharmaceutical composition can be formulated as a gel. In some aspects, the pharmaceutical composition can be formulated as a cream. In some aspects, the pharmaceutical composition can be formulated as an ointment. In some aspects, the pharmaceutical composition can be formulated as a lotion. In some aspects, the pharmaceutical composition can be formulated as an ovule. In some aspects, the pharmaceutical composition can be formulated as a soft capsule. In some aspects, the pharmaceutical composition can be formulated as a suppository. In some aspects, the pharmaceutical composition can be formulated as a pessary. In some aspects, the pharmaceutical composition can be formulated as any combination of the above formulations.

In a preferred embodiment, the formulation is substantially free of pigments, dyes, and/or inks. As used herein, "substantially free" refers to less than 10%, preferably less than 5%, preferably less than 1%, preferably less than 0.1%, and preferably less than 0.05%.

Also disclosed herein are methods of treating a patient having an HPV related dysplasia of the cervix comprising administering to said patient a therapeutically effective dose of the disclosed pharmaceutical compositions.

As used herein, "dysplasia" encompasses pre-invasive lesions and cancer. HPV related pre-invasive lesions include high grade squamous intraepithelial lesion (HSIL), atypical squamous cells of undetermined significance (ASCUS), and low grade squamous intraepithelial lesion (LSIL). HPV related cancers include, for example, cervical intraepithelial neoplasia (CIN) and invasive cervical cancer (ICC).

The disclosed methods can be used to treat HPV related dysplasia. In some aspects, for example, the disclosed methods can be used to treat HSIL. In some aspects, the disclosed methods can be used to treat ASCUS. In other aspects, the disclosed methods can be used to treat LSIL. In other aspects, the disclosed methods can be used to treat CIN. In yet other embodiments, the disclosed methods can be used to treat ICC. Additionally, the disclosed methods can be used to inhibit the progression of HPV related dysplasia. In some aspects, for example, the disclosed methods can be used to inhibit the progression of HSIL. In some aspects, the disclosed methods can be used to inhibit the progression of ASCUS. In other aspects, the disclosed methods can be used to inhibit the progression of LSIL. In other aspects, the disclosed methods can be used to inhibit the progression of CIN. In yet other embodiments, the disclosed methods can be used to inhibit the progression of ICC.

The pharmaceutical composition can reduce the severity of the HPV related dysplasia. Severity of the HPV related dysplasia can be measured and graded by, for example, changes in histology. Methods of performing histology on biopsies of HPV-related lesions are well known in the art. In some embodiments, for example, the disclosed methods can reduce the severity of CIN 3. In some aspects, the disclosed methods can reduce the severity of CIN3 to CIN2. In other aspects, the disclosed methods can reduce the severity of CIN3 to CIN1. In other aspects, the disclosed methods can reduce the severity of CIN3 to HPV negative. In other aspects, the disclosed methods can reduce the severity of CIN2 to CIN1. In other aspects, the disclosed methods can reduce the severity of CIN2 to HPV negative. In other aspects, the disclosed methods can reduce the severity of CIN1 to HPV negative.

In some aspects of the methods, the patient has a cervical cytology (e.g., from a PAP smear) of HSIL, ASCUS, or LSIL. Administration of the pharmaceutical composition to the patient can reduce the cervical cytology. In some aspects, the cervical cytology is reduced from HSIL to a normal cytology. In some aspects, the cervical cytology is reduced from HSIL to ACSUS. In some aspects, the cervical cytology is reduced from HSIL to LSIL. In some aspects, the cervical cytology is reduced from ACSUS to a normal cytology. In some aspects, the cervical cytology s reduced from LSIL to a normal cytology.

Histological assessments to evaluate and/or grade the severity of the HPV related dysplasia and cytological screening can be performed at any suitable time period prior to, during, and/or post-treatment with the disclosed compositions. In some embodiments, the methods further comprise post-treatment monitoring of the patient. Suitable timeframes for post-treatment monitoring include, but are not limited to, 4 weeks, 8 weeks, 12 weeks, 16 weeks, 20 weeks, 24 weeks, 28 weeks, 32 weeks, 36 weeks, 40 weeks, 44 weeks, 48 weeks, or 52 weeks following treatment with the disclosed pharmaceutical compositions. In some aspects, for example, a histological assessment can be performed at baseline (prior to treatment) and 6 months post-treatment to assess changes in CIN status. In other aspects, a cytological screen can be performed at baseline and 6 months post-treatment to assess changes in cervical cytology. In yet other aspects, a histological assessment and cytological screen can be performed at baseline and 6 months post-treatment to assess changes in CIN status and cervical cytology, respectively.

The extent and grade of an HPV related dysplasia can be reduced during a period of from about 4 weeks to about 52 weeks following administering said composition. In some aspects, the extent and histological grade of the dysplasia can be reduced from about 4 weeks to about 46 weeks following administering said composition. In some aspects, the extent and histological grade of the dysplasia can be reduced from about 4 weeks to about 40 weeks following administering said composition. In some aspects, the extent and histological grade of the dysplasia can be reduced from about 4 weeks to about 34 weeks following administering said composition. In some aspects, the extent and histological grade of the dysplasia can be reduced from about 4 weeks to about 28 weeks following administering said composition. In some aspects, the extent and histological grade of the dysplasia can be reduced from about 4 weeks to about 24 weeks following administering said composition. In some aspects, the extent and histological grade of the dysplasia can be reduced from about 4 weeks to about 18 weeks following administering said composition. In some aspects, the extent and histological grade of the dysplasia can be reduced from about 4 weeks to about 12 weeks following administering said composition. In some aspects, the extent and histological grade of the dysplasia can be reduced from about 6 weeks to about 10 weeks following administering said composition. In some aspects, the extent and histological grade of the dysplasia can be reduced from about 8 weeks to about 52 weeks following administering said composition. In some aspects, the extent and histological grade of the dysplasia can be reduced from about 12 weeks to about 52 weeks following administering said composition. In some aspects, the extent and histological grade of the dysplasia can be reduced from about 18 weeks to about 52 weeks following administering said composition. In some aspects, the extent and histological grade of the dysplasia can be reduced from about 24 weeks to about 52 weeks following administering said composition. In some aspects, the extent and histological grade of the dysplasia can be reduced from about 30 weeks to about 52 weeks following administering said composition. In some aspects, the extent and histological grade of the dysplasia can be reduced from about 36 weeks to about 52 weeks following administering said composition. In some aspects, the extent and histological grade of the dysplasia can be reduced about 42 weeks to about 52 weeks following administering said composition. In some aspects, the extent and histological grade of the dysplasia can be reduced from about 48 weeks to about 52 weeks following administering said composition.

In some aspects, the extent and histological grade of the dysplasia can be reduced within about 4 weeks following administering said composition. In some aspects, the extent and histological grade of the dysplasia can be reduced within about 5 weeks following administering said composition. In some aspects, the extent and histological grade of the dysplasia can be reduced within about 6 weeks following administering said composition. In some aspects, the extent and histological grade of the dysplasia can be reduced within about 7 weeks following administering said composition. In some aspects, the extent and histological grade of the dysplasia can be reduced within about 8 weeks following administering said composition. In some aspects, the extent and histological grade of the dysplasia can be reduced within about 9 weeks following administering said composition. In some aspects, the extent and histological grade of the dysplasia can be reduced within about 10 weeks following administering said composition. In some aspects, the extent and histological grade of the dysplasia can be reduced extent and histological grade of the dysplasia can be reduced within about 11 weeks following administering said composition. In some aspects, the extent and histological grade of the dysplasia can be reduced within about 12 weeks following administering said composition. In some aspects, the extent and histological grade of the dysplasia can be reduced within about 16 weeks following administering said composition. In some aspects, the extent and histological grade of the dysplasia can be reduced within about 20 weeks following administering said composition. In some aspects, the extent and histological grade of the dysplasia can be reduced within about 24 weeks following administering said composition. In some aspects, the extent and histological grade of the dysplasia can be reduced within about 28 weeks following administering said composition. In some aspects, the extent and histological grade of the dysplasia can be reduced within about 32 weeks following administering said composition. In some aspects, the extent and histological grade of the dysplasia can be reduced within about 36 weeks following administering said composition. In some aspects, the extent and histological grade of the dysplasia can be reduced within about 40 weeks following administering said composition. In some aspects, the extent and histological grade of the dysplasia can be reduced within about 44 weeks following administering said composition. In some aspects, the extent and histological grade of the dysplasia can be reduced within about 48 weeks following administering said composition. In some aspects, the extent and histological grade of the dysplasia can be reduced within about 52 weeks following administering said composition.

The cervical cytology grade can similarly be reduced from about 4 weeks to about 52 weeks following administering said composition. In some aspects, the cervical cytology grade be reduced from about 4 weeks to about 46 weeks following administering said composition. In some aspects, the cervical cytology grade be reduced from about 4 weeks to about 40 weeks following administering said composition. In some aspects, the cervical cytology grade be reduced from about 4 weeks to about 34 weeks following administering said composition. In some aspects, the cervical cytology grade be reduced from about 4 weeks to about 28 weeks following administering said composition. In some aspects, the cervical cytology grade be reduced from about 4 weeks to about 24 weeks following administering said composition. In some aspects, the cervical cytology grade be reduced from about 4 weeks to about 18 weeks following administering said composition. In some aspects, the cervical cytology grade be reduced from about 4 weeks to about 12 weeks following administering said composition. In some aspects, the cervical cytology grade be reduced from about 6 weeks to about 10 weeks following administering said composition. In some aspects, the cervical cytology grade be reduced from about 8 weeks to about 52 weeks following administering said composition. In some aspects, the cervical cytology grade be reduced from about 12 weeks to about 52 weeks following administering said composition. In some aspects, the cervical cytology grade be reduced from about 18 weeks to about 52 weeks following administering said composition. In some aspects, the cervical cytology grade be reduced from about 24 weeks to about 52 weeks following administering said composition. In some aspects, the cervical cytology grade be reduced from about 30 weeks to about 52 weeks following administering said composition. In some aspects, the cervical cytology grade be reduced from about 36 weeks to about 52 weeks following administering said composition. In some aspects, the cervical cytology grade be reduced from about 42 weeks to about 52 weeks following administering said composition. In some aspects, the cervical cytology grade be reduced from about 48 weeks to about 52 weeks following administering said composition.

In some aspects, the cervical cytology grade reduced within about 4 weeks following administering said composition. In some aspects, the cervical cytology grade reduced within about 5 weeks following administering said composition. In some aspects, the cervical cytology grade reduced within about 6 weeks following administering said composition. In some aspects, the cervical cytology grade reduced within about 7 weeks following administering said composition. In some aspects, the cervical cytology grade reduced within about 8 weeks following administering said composition. In some aspects, the cervical cytology grade reduced within about 9 weeks following administering said composition. In some aspects, the cervical cytology grade reduced within about 10 weeks following administering said composition. In some aspects, the cervical cytology grade reduced within about 11 weeks following administering said composition. In some aspects, the cervical cytology grade reduced within about 12 weeks following administering said composition. In some aspects, the cervical cytology grade reduced within about 16 weeks following administering said composition. In some aspects, the cervical cytology grade reduced within about 20 weeks following administering said composition. In some aspects, the cervical cytology grade reduced within about 24 weeks following administering said composition. In some aspects, the cervical cytology grade reduced within about 28 weeks following administering said composition. In some aspects, the cervical cytology grade reduced within about 32 weeks following administering said composition. In some aspects, the cervical cytology grade reduced within about 36 weeks following administering said composition. In some aspects, the cervical cytology grade reduced within about 40 weeks following administering said composition. In some aspects, the cervical cytology grade reduced within about 44 weeks following administering said composition. In some aspects, the cervical cytology grade reduced within about 48 weeks following administering said composition. In some aspects, the cervical cytology grade reduced within about 52 weeks following administering said composition.

The therapeutically effective dose of the disclosed pharmaceutical compositions can be administered for about 1 week to about 4 weeks. After this time a clinician may assess whether the course of treatment has been successful. A decision may then be made whether or not to continue treatment.

It will be appreciated that a clinician may wish to take into account menstruation when deciding on a treatment regimen for conditions relating to the cervix. Accordingly, a preferred treatment regimen may be for about 14-21 days and can be administered between menses. A clinician may elect to stop topical treatment of the cervix during menses and recommence a new course of treatment in the next menstrual cycle. By way of example, a preferred treatment regimen can be: (1) 14-21 days of administration; (2) followed by 1-14 days without treatment (during which menses may occur if treating the cervix); and (3) a further cycle of 14-21 days of treatment if this is considered medically necessary. In a most preferred embodiment, the cervix of a women may be treated such that she receives about 266.6 mg of lopinavir and about 66.6 mg ritonavir per day for 14-21 days; treatment can then be stopped for 1-14 days and a clinical reassessment can be conducted; then, if necessary a second treatment cycle of about 533 mg of lopinavir and about 126 mg ritonavir per day can be administered for a further 14-21 days. After the second cycle a further clinical assessment can be made and a decision made about whether or not subsequent treatment cycles are required.

Unexpectedly, one treatment cycle of 14 days is very effective for eradicating oncogenic viral infection and reducing or eradicating precancerous or cancerous lesions (see the Examples).

By way of further example, and without intending to be limiting, a preferred treatment regimen for treating the cervix of a woman in need of treatment can be: (1) 14-21 days of administration; (2) optionally followed by 1-14 days without treatment (during which menses may occur); and (3) a further cycle of 14-21 days of treatment if this is considered medically necessary. The women may be treated such that she receives between about 400 mg and about 600 mg of lopinavir and between about 100 mg and about 150 mg ritonavir per day as a single vaginal dose which is ideally self-administered last thing at night (i.e. just before retiring for sleep).

In some embodiments, the composition can be administered twice daily for 14 days.

In some embodiments, the composition induces apoptosis of HPV infected cells.

EXAMPLES

Example 1—Combination of Lopinavir and Ritonavir are Useful for Preventing or Treating Malignant Conditions Caused by HPV Infections Experiments were conducted to demonstrate that a combination of lopinavir and ritonavir were useful for preventing or treating malignant conditions caused by HPV infections. Lopimune (Kaletra®) soft gel capsules were used to illustrate the efficacy of lopinavir and ritonavir combination therapy.

Experimental Methods

Patient Characteristics:

Subject to approval by Kenyatta National Hospital Ethics board, more than 800 Kenyan women were provided with the opportunity for a free Human Papillomavirus (HPV) test (Cervista® HR Hologic Inc., USA) followed by a liquid based cervical (LBC) cytology test (ThinPrep®, Hologic Inc., USA). Study subjects were recruited from patients attending Kenyatta National Hospital's Family Planning Clinic and Gynaecology Out-patient Clinics in Nairobi according to the following criteria:

Inclusion:
1. Must be aged above 18 yrs.
2. Freely agreed to join the study after extensive information and counselling and agreed to give written informed consent.
3. Were capable of receiving and understand verbal and written information about the study.
4. Ready and willing to comply with the study follow-up schedule.

Exclusion:
1. Under 18 yrs of age.
2. Do not fulfil the above inclusion criteria.
3. Pre-existing conditions in which blood sampling may increase risk of complications e.g. sickle cell disease.
4. A positive HIV test.
5. Patients who are too ill to give informed consent.

ThinPrep® LBC samples were collected from >800 women who satisfied the above inclusion criteria in Nairobi between 1$^{st}$ Mar. and 30$^{th}$ Aug. 2013 and these were shipped to the University of Manchester for laboratory analysis.

The Cervista® HPV Test:

The Cervista® HR HPV test identifies whether any of 14 different high-risk types of HPV (Types 16, 18, 31, 33, 35, 39, 45, 51, 52, 56, 58, 59, 66, 68) are present and was the first test of its type to be approved by the FDA. The Cervista® HPV HR test does not determine the specific type of high risk HPV present.

The Cervista® medium Throughput Automation (MTA) machine is a fully automated CPU controlled device providing a 'sample in—results out' system with minimal user input. Using 2 ml of cervical smear sample, stored in ThinPrep® Pap Test PreservCyt® solution the Cervista®MTA initially carries out a fully automated DNA extraction before placing the extracted ultra-pure DNA into a 96-well assay plate. Subsequently using the ultra-pure DNA, the Cervista®MTA sets up the Cervista®HPV HR assay which uses Invader® chemistry, a FRET-based signal amplification method for the detection of specific nucleic acid sequences. By combining HPV specific signals with control housekeeping reference sequences, the system is fully internally controlled and validated.

It is based on signal rather than DNA amplification technology and is 100% effective at detecting high-grade squamous intraepithelial lesions (HSIL) of the cervix. Genomic DNA was extracted as described and applied to the Cervista® machine.

Liquid Based Cytology:

ThinPrep® LBC slides were then prepared using the Hologic Thinprep T2000 Processor from all women. These were then processed with an automated staining system for papanicolaou staining and cover-slipping at Central Manchester NHS Regional Cytology Laboratories. LBC slides from women identified by Cervista® as positive for high-risk HPV were then scanned using the ThinPrep Dual Review Imager with final cytology reporting carried out by a consultant cytopathologist (Dr Mina Desai CBE).

Treatment with Lopimmune (CIPLA) (Kaletra, Abbvie) Soft Gel Capsules:

Women identified as Cervista® positive for high-risk types of HPV who were also identified as being positive for HSIL, or low grade disease (LSIL), were enrolled as study participants. They were then examined by colposcopy and photographed (Welch Allyn Video Colposcope) using visual inspection with Lugol's iodine (VILI—Also known as Schiller's test). VILI identifies the extent of pre-cancerous lesions which appear bright yellow saffron in colour whereas normal squamous epithelium appears dark brown. They were subsequently given a supply of Lopimmune soft gel capsules (normally prescribed for oral administration) to cover a treatment period of two weeks administering 1 capsule twice daily as an intra-vaginal pessary over this period during which they were asked to refrain from sexual activity. Furthermore, women were interviewed routinely during the treatment period for any adverse reactions such as itching, inflammation etc. Two weeks after the two-week treatment had finished, women were recalled, examined by colposcope with VILI, re-photographed and a ThinPrep® LBC sample collected which was sent to Manchester for Cervista® HR HPV testing and cervical cytology as described previously.

Two months later women were re-called, examined by colposocope plus VILI, re-photographed and ThinPrep® LBC samples again collected. In addition, punch biopsies were also taken and fixed in formalin. This material was then sent to Manchester for Cervista® HR HPV testing plus ThinPrep® cervical cytology on LBC's whereas the punch biopsies were wax embedded and assessed by histopathology.

Results

FIGS. 1A, B, C & D show VILI staining plus HPV status and the cytology report of representative examples before and after treatment with Lopimmune as a pessary and Table 2 summaries the results for 18 patients on the trial.

TABLE 2

Summary of Lopimmune Treatment Results

| Pre-Treatment Diagnosis | Post-Treatment Cytology | | Post-Treatment HPV Status | |
|---|---|---|---|---|
| | 1 Month | 3 Months | 1 Month | 3 Month |
| (1) HPV+ve HSIL | Normal | Normal | Negative | Negative |
| (2) HPV+ve HSIL | HSIL | Normal | Negative | Negative |
| (3) HPV+ve HSIL | Normal | HSIL | Positive | Positive |
| (4) HPV+ve HSIL | Normal | Normal | Negative | Negative |
| (5) HPV+ve LSIL | Normal | Normal | Negative | Negative |
| (6) HPV+ve HSIL | HSIL | HSIL | Positive | Positive |
| (7) HPV+ve HSIL | HSIL | LSIL | Positive | Positive |
| (8) HPV+ve HSIL | HSIL | ND | Positive | ND |
| (9) HPV+ve HSIL | HSIL | Borderline | Positive | Negative |
| (10) HPV+ve HSIL | HSIL | ND | Positive | ND |
| (11) HPV+ve HSIL | Normal | ND | Negative | ND |
| (12) HPV+ve HSIL | Normal | ND | Positive | ND |
| (13) HPV+ve HSIL/LSIL | Normal | ND | Negative | ND |
| (14) HPV+ve HSIL | Normal | ND | Positive | ND |
| (15) HPV+ve HSIL | Normal | ND | Negative | ND |
| (16) HPV+ve HSIL | Normal | ND | Negative | ND |
| (17) HPV+ve HSIL | Normal | ND | Positive | ND |
| (18) HPV+ve HSIL | Normal | ND | Negative | ND |

ND = Not determined at this time.

To date, 11 out of 17 patients (65%) diagnosed as Cervista HPV+ve with HSIL prior to treatment became cytologically normal 1 month after the start of Lopimmune treatment. Patient 5 was diagnosed with HPV+ve LSIL prior to treatment and was cytologically normal 1 and 3 months after the start of Lopimmune treatment. Six patients with HSIL (No's 2, 6, 7, 8, 9 & 10) showed no improvement in cytology at 1 month although two of these (2 & 9) subsequently became negative for HPV with normal or borderline cytology at 3 months and 7 became LSIL at 3 months. One patient with HSIL (No 3) was cytologically normal but still positive for HPV at 1 month and was subsequently diagnosed with HSIL at 3 months. 8 out of 18 (44%) of patients became Cervista HPV negative at 1 month and although one of these (No 9) was HPV+ve at 1 month, this patient later became negative at 3 months.

In summary, 15 out of the 18 (85%) of the patients treated showed either normalisation or improved cytology during the 3 month follow up and only one of these regressed to HSIL during this period. Out of the 16 who responded 10 patients (66%) became HPV negative during this period Conclusions There were no adverse reactions reported from any of the patients treated. One Lopimmune soft gel capsule administered as a pessary twice a day for two weeks is effective for curative treatment of some HPV positive HSIL lesions within one to three months of commencing treatment as exemplified by FIGS. 1A & B. At this dose, some patients became HPV negative at one month with HSIL cytology which later became normal cytology at three months (FIG. 1C). At this dose, HPV positive treated LSIL lesions became HPV negative and cytology normal at one month (FIG. 1D).

Table 2 summarises the results showing that Lopimune (KALETRA®) soft gel capsules have a pronounced curative effect against HPV infection of the cervix, and the lesions this causes, when administered at a dose of 1 capsule (or equivalent drug content) twice a day for a period of 2 weeks.

Example 2—Expansion and Refinement of the Trials Described in Example 1

Methods

Patients and Study Centres:

Clinical and basic diagnostic tests were done at University of Nairobi/Kenyatta National Hospital (KNH), Kenya while scientific aspects of the study that required specialized equipment were carried out at the Viral Oncology Laboratory, St Marys Hospital in Manchester, UK. The trial was conducted between Jan. 3, 2013 and Jan. 11, 2013 and patients were recruited from women attending the Family Planning and Gynaecology Outpatient clinic at K.N.H. for routine follow up.

Enrollment and Procedures:

The study protocol is illustrated in FIG. 2. Briefly, at the screening stage, potential participants were given the patient information sheet, counselled appropriately and those willing to participate gave informed signed consent. Thereafter, a questionnaire was used to take both the socio-demographic, sexual histories and clinical characteristics. Blood was drawn for a HIV test using Determine™ (Abbott, USA) and if positive was confirmed by Unigold™ (Trinity Biotech, Ireland). All patients were then given a speculum examination during which two cervical cyto-brushes samples were taken. The first of these was used for LBC ThinPrep® and HPV testing and samples were immediately sent to Manchester. The second was used for a conventional smear test as per standard Pap smear screening procedures which was examined and reported in Nairobi. Patients were then reviewed after one month at which time those that were HIV negative and HPV positive with abnormal cervical cytology were enrolled into the Lopimune trial.

At enrollment, a pelvic examination was carried out which included baseline colposcopy. Cervical morphology was initially visualised with acetic acid (VIA) followed by Lugol's Iodine (VILI) using ×5 magnification (Video Coloposcope, Welch Allyn. N.Y. USA). This was carried out according to standard clinical practices and images recorded (Sankaranarayanan R et al. Int J Cancer. 2003 Sep. 1; 106(3):404-8). Blood was drawn for a full blood count, urea, creatinine, electrolytes and liver function tests.

Each patient was then issued with a supply of Lopimune soft gels (CIPLA, India) for vaginal insertion of one capsule twice daily for 2 weeks. Two additional visits per week were scheduled for the two week duration of Lopimune therapy during which a questionnaire was filled out to assess occurrence of adverse drug reactions and drug compliance. Enrolled patients had serial visits scheduled at 1, 2, 4, 8, 12 and 16 weeks. Follow up LBC ThinPrep® samples were taken at 4 and 12 weeks and sent to Manchester for cytology and HPV testing. In addition, colposcopy with VILI was carried out at 4 and 12 weeks and final punch biopsies were taken at the latter time point. Blood was also drawn at these visits for baseline clinical tests as described previously. The 8 week visit was to assess any potential drug reactions and to remind women that a punch biopsy would be taken from any abnormal areas detected by VIA or VILI on the cervix at the 12 week visit. Biopsies were stored in 10% buffered formalin and were sent to Manchester. Those patients diagnosed with post-treatment, HPV positive high-grade disease were referred for Loop electrosurgical excision procedure (LEEP). These were reviewed again at 5 months and advised to continue routine Pap smear screening at 6 months thereafter.

Cervista® HR-HPV Test:

All ThinPrep® LBC samples sent to Manchester were analysed by staff trained and certified by Hologic (Hologic, Bedford, Mass.). HPV testing of LBC samples was carried out using the FDA-approved Cervista HPV HR test (Day et al. J Clin Virol. 2009 July; 45 Suppl 1:S63-72) in conjunction with the Cervista MTA (Hologic) automated platform according to the manufacturer's instructions. This system provides ultra-pure DNA extraction and HPV testing in one sealed unit requiring no user input following initiation. In brief, Cervista uses three proprietary oligonucleotide probe master-mixes, designed to detect 14 high risk HPV types within three familial groups based on phylogenetic similarities: Mix 1 detects types 51, 56, and 66; Mix 2 detects types 18, 39, 45, 59 and 68; Mix 3 detects types 16, 31, 33, 35, 52, and 58. A separate human histone 2 gene probe serves as an internal control for cellular DNA content within the LBC sample. A HPV positive signal is indicated by fluorescent signal above an empirically derived cut-off value. Prior to and after analysis, all LBC samples were stored at +4° C. in a monitored refrigerator.

HPV Genotyping:

Ultrapure DNA isolated from each ThinPrep® LBC sample which was used for the Cervista® test, was then further analysed by PCR to test for which HPV genotypes were present in each respective Cervista mastermix positive sample. A novel hot-start, touch-down multiplex method was used which simultaneously detects the L1, E6 and E7 ORFs of HPV type 16, 18, 31, 33, 35, 39, 45, 51, 52, 56, 58, 59, 66, 68, and 70 as described in Maranga et al. (Open Virol J. 2013; 7:19-27). Each assay was repeated a minimum of three times.

LBC ThinPrep® Cervical Cytology:

LBC slide preparation was carried out using the ThinPrep-2000 system (Hologic) automated slide preparation unit, according to the manufactures directions and Pap stained (Hologic) at the Regional Cytology Laboratories (Clinical Sciences Building, Manchester Royal Infirmary, UK). LBC reporting was carried out by Dr M Desai using a Dual Review Imaging System (Hologic).

Cervical Pathology:

Final 3 mm punch biopsy samples of the cervical transformation zone and VILI positive lesions were transported to Manchester, wax embedded and 3-4 μm sections cut at 3 levels according to standard pathology laboratory practices. The sections were then stained with haematoxylin and eosin and reported separately by two pathologists (Dr MP Okemwa—Kenya and Dr H Stringfellow—a specialist gynaecological pathologist in the UK). Cases where there was disagreement were independently reviewed by a third gynaecological pathologist (Dr B. Da Gama-Rose).

Resuylts

Primary HPV and Cytology Screening:

Out of 805 HIV negative women given the Cervista HR-HPV test, 164 (20.4%) were positive for high-risk HPV.

Out of these, cytology showed that 28 (17.1%) had HSIL, 11 (6.7%) had LSIL and 21 (12.8%) had ASCUS. Five (3.0%) were diagnosed with ICC and were sent for immediate biopsy and subsequent treatment (hysterectomy). The finding that 20.4% of Kenyan women were positive for HR-HPV with an overall incidence of 3.5% for HSIL was entirely consistent with a reported study (Maranga et el. supra) and would be predicted from an unscreened population of this type. Out of the 28 women identified with HSIL, 5 were lost to follow up with 23 eventually being enrolled on the trial. In light of this, an additional 17 women with either ASCUS or LSIL were also recruited to increase the power of the study.

Table 3 shows the results of the primary Cervista® HR-HPV test, HPV PCR genotype analysis, ThinPrep® LBC and conventional smear tests that were carried out on the 23 women diagnosed with HSIL. When combined, a relatively high incidence of HPV types 16 and 18 were detected which together amounted to 10/23 (43.5%) of cases. With 5 infections, type 52 was the next most common followed by 4 infections each for types 35, 58 and 33. On one occasion (E02) Cervista® detected a positive for more than one master mix whereas PCR only detected one HPV genotype present which could be due to differences in sensitivity between these methods. A good concordance between HSIL diagnosed by LBC in Manchester and conventional smear testing carried out in Kenya was observed with only 3/23 disparities. Patients E1 and E11 were diagnosed with ASC-H by conventional cytology and E7 with LSIL.

TABLE 3

Patient characteristics of women diagnosed with HSIL prior to treatment

| E-No | Birth Control | Parity | Age | HPV status Cervista | PCR | LBC | Conventional smear |
|---|---|---|---|---|---|---|---|
| E01 | Cond | 2 + 1 | 29 | M3 | 35 | HSIL | ASC-H/AGC |
| E02 | TL | 2 + 0 | 39 | M1, 3 | 52 | HSIL | HSIL |
| E03 | None | 2 + 0 | 35 | M3 | 16 | HSIL | HSIL |
| E04 | IUD | 4 + 0 | 42 | M1 | 70 | HSIL | HSIL |
| E06 | None | 2 + 0 | 29 | M2, 3 | 16, 39 | HSIL | HSIL |
| E07 | IUD | 2 + 1 | 23 | M2, 3 | 18, 52 | HSIL | LSIL |
| E08 | None | 2 + 0 | 27 | M3 | 52 | HSIL | HSIL |
| E09 | IUD | 2 + 0 | 38 | M2 | 18 | HSIL | HSIL |
| E10 | None | 2 + 0 | 37 | M2 | 45 | HSIL | HSIL |
| E11 | None | 2 + 0 | 37 | M3 | 33, 58 | HSIL | ASC-H |
| E12 | IUD | 2 + 0 | 41 | M2 | 18 | HSIL | HSIL |
| E13 | None | 0 + 0 | 22 | M3 | 33, 58 | HSIL | HSIL |
| E14 | None | 0 + 0 | 26 | M3 | 52 | HSIL | HSIL |
| E15 | Depo | 3 + 0 | 40 | M2 | 68 | HSIL | HSIL |
| E16 | Cond | 2 + 0 | 41 | M3 | 52 | HSIL | HSIL |
| E17 | None | 2 + 0 | 38 | M1, 3 | 16, 31, 51 | HSIL | HSIL |
| E18 | IUD | 2 + 0 | 36 | M3 | 33 | HSIL | HSIL |
| E19 | PM | 7 + 0 | 69 | M3 | 58 | HSIL | HSIL |
| E20 | Depo | 1 + 1 | 22 | M3 | 33, 58 | HSIL | HSIL |
| E21 | None | 0 + 1 | 26 | M3 | 16 | HSIL | HSIL |
| E22 | Depo | 6 + 0 | 43 | M3 | 16, 35 | HSIL | HSIL |
| E23 | Jadelle | 2 + 0 | 27 | M3 | 16, 35 | HSIL | HSIL |
| E29 | Depo | 5 + 0 | 47 | M3 | 16, 35 | HSIL | HSIL |

Table 4 shows the same data for the 17 women initially diagnosed with LSIL/ASCUS and demonstrates greater variation between LBC based diagnosis and conventional smear testing where 5/17 differential diagnosis were reported. HPV genotype analysis showed 6/17 (35.4%) were positive for types 16 and 18 followed by type 35 with 5 positives, type 56 with 4 positives and types 58 and 33 both with 3 positives. Curiously two samples (E33 and E40) were Cervista Mix 1 positive but PCR failed to detect any of the Mix 1 genotypes which again could be related to sensitivity. The average age of women in table 3 was 34.22 yrs and 33.76 yrs for table 4.

TABLE 4

Patient characteristics of women diagnosed with ASCUS/LSIL prior to treatment

| E. No | Birth Control | Parity | Age | HPV status Cervista | PCR | LBC | Conventional smear |
|---|---|---|---|---|---|---|---|
| E05 | Depo | 3 + 0 | 41 | M2 | 18 | LSIL | LSIL |
| E24 | None | 3 + 0 | 48 | M3 | 16, 35 | LSIL | HSIL |
| E25 | IUD | 3 + 0 | 46 | M1, 3 | 33 | ASCUS | ASCUS |
| E27 | e-pill | 1 + 1 | 25 | M3 | 33, 58 | LSIL | HSIL |
| E28 | Cond | 0 + 1 | 23 | M2, 3 | 35, 45, 66 | LSIL | LSIL |
| E30 | Cond | 3 + 0 | 30 | M3 | 16, 35 | ASCUS | ASCUS |
| E31 | None | 3 + 0 | 37 | M1 | 51 | LSIL | LSIL |
| E32 | None | 0 + 1 | 27 | M3 | 16, 52 | ASCUS | ASCUS |
| E33 | None | 1 + 0 | 26 | M1 | N | ASCUS | HSIL |
| E34 | None | 4 + 0 | 56 | M1, 3 | 56, 58 | LSIL | LSIL |
| E35 | None | 2 + 0 | 32 | M3 | 16, 31 | ASCUS | ASCUS |
| E36 | None | 0 + 0 | 21 | M1 | 56 | ASCUS | ASCUS |
| E37 | None | 2 + 0 | 43 | M1 | 56 | ASCUS | ASCUS |
| E38 | Depo | 3 + 0 | 27 | M3 | 33, 35, 58 | ASCUS | Normal |
| E39 | IUD | 2 + 0 | 32 | M3 | 16, 35 | LSIL | LSIL |
| E40 | None | 0 + 0 | 26 | M1 | N | ASCUS | ASCUS |
| E41 | IUD | 3 + 1 | 42 | M1 | 56 | ASCUS | LSIL |

M1: Cervista Mix 1 (M1) (HPV 51, 56, 66, or 70)
M2: Cervista Mix 2 (M2) (HPV 18, 39, 45, 59, 68)
M3: Cervista Mix 3 (M3) (HPV 16, 31, 33, 35, 52, 58)
ASCUS: Atypical squamous cells of undetermined significance
ASC-H: Atypical squamous cells - cannot exclude HSIL
AGC: Atypical glandular cells
N: Negative
Depo: Depoprovera
TL: Tubal ligation
PM: Post menopausal
None of the women smoked.

Lopimune Treatment of Women Initially Diagnosed with HSIL:

All of the women shown in table 3 were given a two week course of 1 capsule of Lopimune twice daily, self-administered as a vaginal suppository. During this treatment period interviews carried out every 2 days reported no adverse reactions such as unusual vaginal sensations, discharge, vaginitis, cervicitis, vulvitis, itching, burning, vaginal dryness or numbness. Repeat follow up baseline clinical tests carried out at 1, 2 and 4 weeks post-treatment also revealed no cause for concern.

Figure 3:
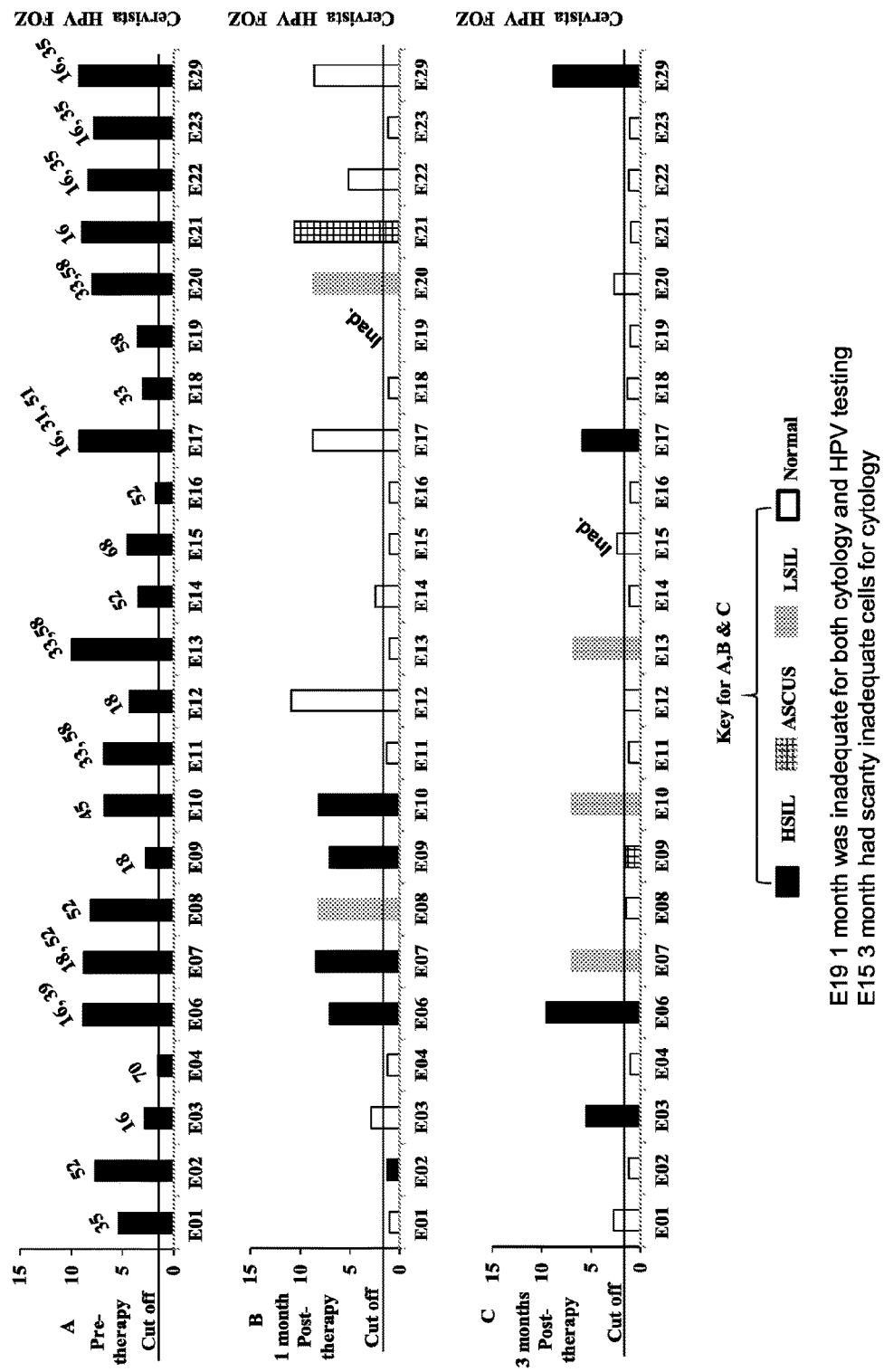
FIG. 3, comprising

The results of repeat ThinPrep® LBC and Cervista® HPV tests carried out at 4 and 12 weeks post-start of treatment are summarised in FIGS. 3A, B and C where the HPV genotypes present are shown above each bar. The height of the bar indicates the level of HPV detected in each patient and demonstrates that a post-treatment drop in the levels of HPV infection was observed in 19/23 (82.6%) with the virus not detected in 12/23 (52.2%) of women 12 weeks after the start of treatment.

After only 4 weeks (FIG. 3B) 14/22 (63.6%) of patients had returned to normal cytology and 3/22 (13.6%) now had lower grade disease demonstrating a positive response in 76.9% of women. After 12 weeks (FIG. 3C) 14/22 (63.6%) of women still had normal cytology with 4/22 (18.2%) now presenting with lower grade dysplasia providing an overall positive response in 81.8% of women. A total of 22 patients were reported at 4 and 12 weeks since E19 had inadequate cellularity for HPV testing and cytology at 4 weeks whereas E15 was adequate for HPV testing but not cytology at 12 weeks.

Table 5 compares the histopathology results with both cytology and the Cervista HPV test. It can be seen that 13/22 (59.1%) had no detectable neoplasia and 4/22 (18.2%) had CIN1 which potentially demonstrates a 77.3% positive response to treatment. Only 4/22 (18.2%) had CIN2 or CIN3 and 1/22 (4.5%) had hCGIN. A total of 22 patients were reported for pathology since the biopsies obtained from E19 at 12 weeks were not suitable.

TABLE 5

Treatment outcome of women with Pre-Treatment HSIL at 3 Months

| E-No | 3 Month Cytology | 3 Month Cervista | Histopath. (MPO) | Histopath. (HS) |
|---|---|---|---|---|
| E01 | Negative | Positive | None | None |
| E02 | Negative | Negative | None | CIN2* |
| E03 | HSIL | Positive | None | CIN1 and HCGIN* |
| E04 | Negative | Negative | None | None |
| E06 | HSIL (mod) | Positive | CIN1 | CIN1 just |
| E07 | LSIL | Positive | CIN2 | CIN1 – CIN2 |
| E08 | Negative | Negative | None | CIN1* |
| E09 | ASCUS | Negative | None | None |
| E10 | LSIL (mild) | Positive | None | None |
| E11 | Negative | Negative | None | None |
| E12 | Negative | Positive | None | None |
| E13 | LSIL (mild) | Positive | CIN1 | CIN1 – CIN2* |
| E14 | Negative | Negative | None | None |
| E15 | Inadequate | Positive | None | None |
| E16 | Negative | Negative | None | None |
| E17 | HSIL (mod) | Positive | CIN3 | CIN2 + CIN3 |
| E18 | Negative | Negative | None | None |
| E19 | Negative | Negative | Not suitable | Not suitable |
| E20 | Negative | Positive | None | None |
| E21 | Negative | Negative | None | CIN1 just* |
| E22 | Negative | Negative | None | None |
| E23 | Negative | Negative | None | None |
| E29 | HSIL (sev) | Positive | None | CIN1* |

Note:
Diagnosis marked with * were confirmed by a $3^{rd}$ gynaecological pathologist Lopimune Treatment of Women Initially Diagnosed with ASCUS/LSIL:

As for the patients diagnosed with HSIL, all of the women shown in table 4 were given a two week course of 1 capsule of Lopimune twice daily, self-administered as a vaginal suppository and no adverse reactions were reported.

Figure 4:
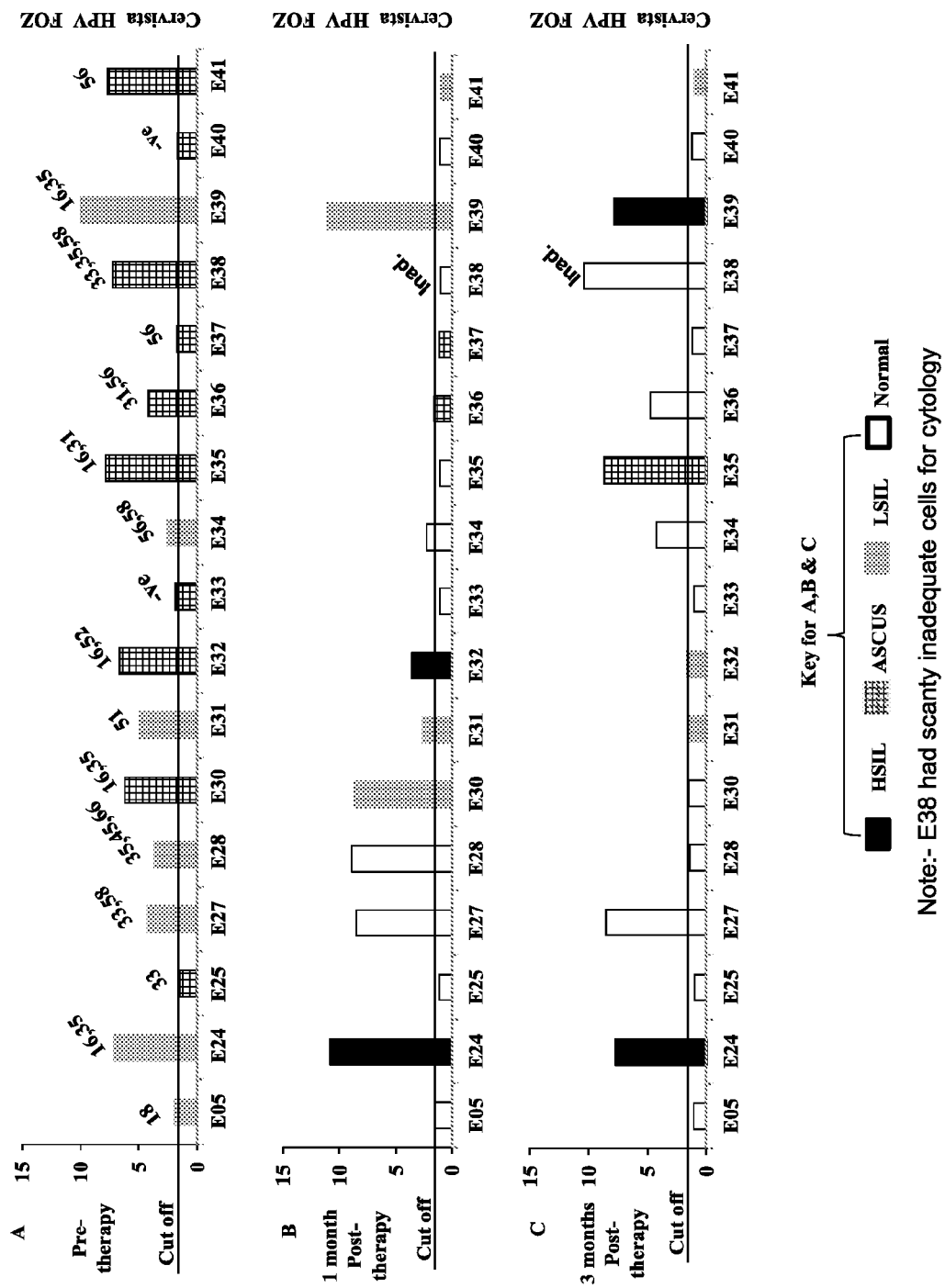
FIG. 4, comprising

The results of repeat ThinPrep® LBC and Cervista® HPV tests carried out at 4 and 12 weeks post-start of treatment are shown in FIGS. 4A, B and C. A post-treatment drop in the levels of HPV infection was observed in 11/17 (65.7%) with the virus not detected in 7/17 (41.1%) of women 12 weeks after treatment.

Out of 16 satisfactory LBC slides, 8 (50%) had returned to normal cytology, 6 (35.3%) still had ASCUS or LSIL and 2 (12.5%) were reported with HSIL after 4 weeks (FIG. 4B). After 12 weeks it can be seen that 10/16 (62.5%) of women had normal cytology, 4/16 (25.0%) ASCUS or LSIL and 2/16 (12.5%) now had HSIL (FIG. 4C).

Table 6 shows comparison of the histopathology results with both cytology and the Cervista HPV test. It can be seen that 9/17 (52.9%) had no evidence of neoplasia, 6/17 (35.3%) had CIN1 and 2/17 (11.8%) had CIN1/2.

TABLE 6

Treatment outcome of women with Pre-Treatment LSIL/ASCUS at 3 Months

| E-No | 3 Month Cytology | 3 Month Cervista | Histopath (MPO) | Histopath (HS) |
|---|---|---|---|---|
| E05 | Negative | Negative | CIN1 | CIN1* |
| E24 | HSIL (sev) | Positive | None | None |
| E25 | Negative | Negative | None | CIN1* |
| E27 | Negative | Positive | None | None |
| E28 | Negative | Negative | CIN1 | CIN1 |
| E30 | Negative | Positive | None | None |
| E31 | LSIL (mild) | Negative | None | CIN1* |
| E32 | LSIL (mild) | Positive | None | None |
| E33 | Negative | Negative | None | None |
| E34 | Negative | Positive | CIN2 | CIN1* |
| E35 | ASCUS | Positive | None | None |
| E36 | Negative | Positive | CIN1 – CIN2 | CIN1 + CIN2 |
| E37 | Negative | Positive | None | None |
| E38 | Inadequate | Positive | None | None |
| E39 | HSIL (sev) | Positive | CIN1 | CIN1 + CIN2* |
| E40 | Negative | Negative | None | None |
| E41 | ASCUS | Negative | CIN1 | CIN1 just |

Figure 5:
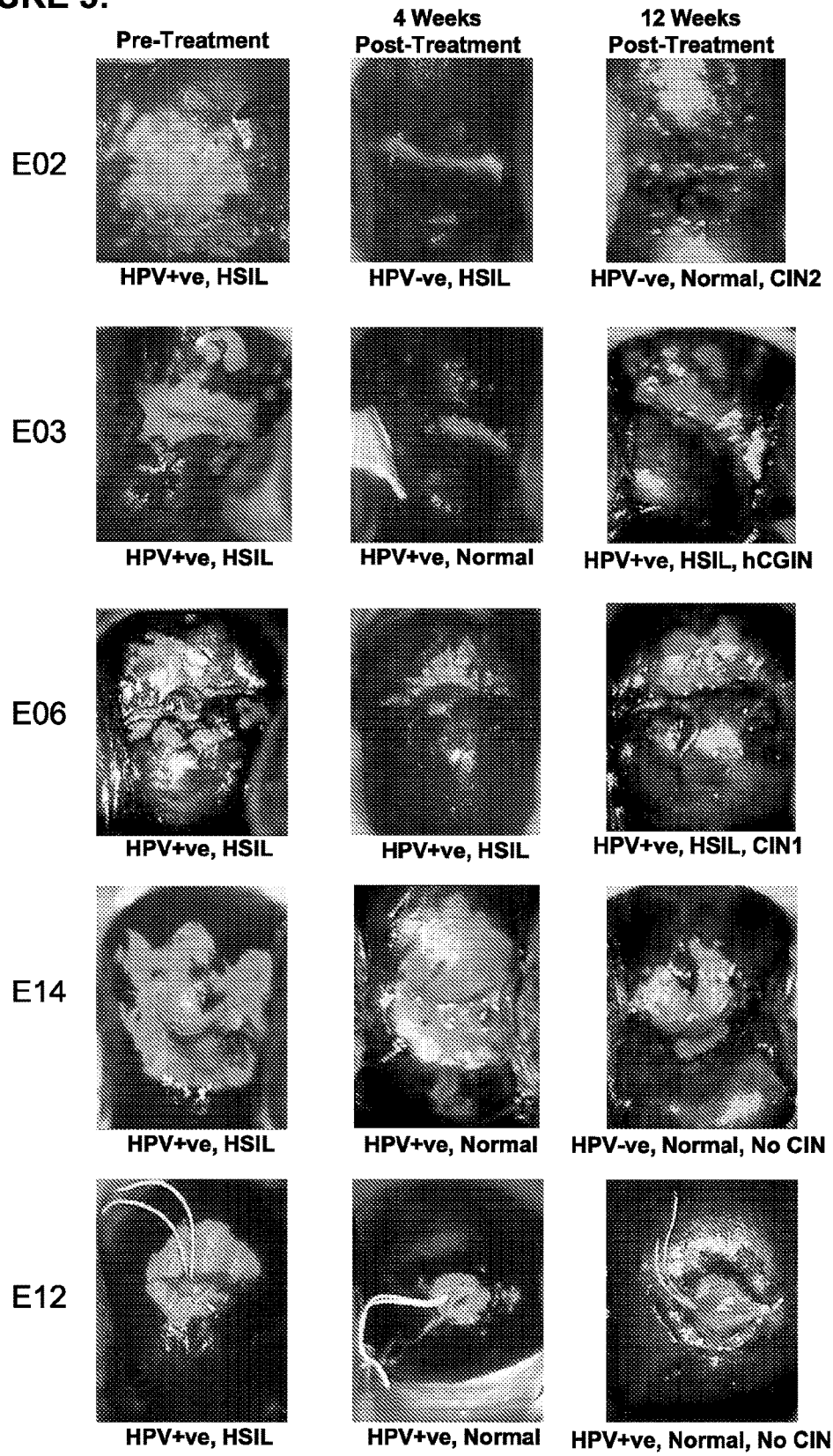
FIG. 5 illustrates the results of colposcopy with VILI before (left column), 4 weeks (middle column) and 12 weeks (right column) after treatment of patients E02, E03, E06, E14 and E12 in Example 2. Magnification ×5 was used with the Cervista® HPV status and cytology shown under each picture and final pathology (CIN status) also shown under the 12 weeks post-treatment images.

Note:
Diagnosis marked with * were confirmed by a $3^{rd}$ gynaecological pathologist Colposcopy with VILI:

FIG. 5 shows VILI colposcopic images of the cervix from 5 cases diagnosed with HSIL taken before, 4 and 12 weeks after treatment with Lopimune capsules. Extensive yellow/orange staining characteristic of poorly glycogenated dysplastic epithelium, was clearly present in all the pre-treatment images of the ectocervix and the cases shown were deliberately chosen to illustrate that types of response observed. The majority of patients showed a reduction in dysplastic epithelium, as detected by VILI, which was associated with reduced severity of disease as indicated by HPV, cytology and/or pathology status. For example, patient E02 became HPV negative at 4 and 12 weeks and also clearly showed a marked regression of dysplastic epithelium detected by VILI although a small focus of CIN2 was still present. Patient E03 remained HPV positive at 4 and 12 weeks with normal cytology at 4 weeks and yet showed HSIL cytology with CIN1 and hCGIN at 12 weeks. E06 remained HPV positive with HSIL cytology after 12 weeks although pathology subsequently showed this to be CIN1. E14 and E12 both showed return to normal cytology at 4 and 12 weeks with no CIN present at 12 weeks although E12 remained HPV positive.

Discussion

It was essential to have a suitable formulation for vaginal delivery of drug directly to the cervix in order to translate the preclinical observations into clinical trials. When used for oral HIV therapy, lopinavir is normally co-adminstered in a 4:1 ratio with ritonavir (Lopimune—CIPLA; Kaletra—Abbvie). It was decided, due to cost and supply issues, to refrain from specifically reformulating lopinavir for vaginal use and the inventors opted to use the commercially available, orally-administered gelatine capsule form of the drug Lopimune as a vaginal suppository.

A maximum dose of twice daily for two weeks was chosen on the basis of ease-of-application and likely patient compliance since the primary objective of this study was to evaluate tolerability and any adverse reactions. HSIL was chosen as the primary disease indication as this is the most persistent type of HPV-related pre-invasive cervical lesion. Indeed, although a proportion of high-risk HPV positive HSIL can regress to normal if left untreated, previous work has shown that the mean time for this to occur is approximately 18-30 months. Moreover, HPV infections are known to be much more persistent when HSIL is present.

In order to identify approximately 30 women with HSIL, previous work had indicated it would be necessary to screen 600-800 women for this purpose (Maranga et al. supra). The actual number screened was 821 and the Cervista® HPV-HR test was used as a primary screen followed by LBC and conventional cytology testing. Cytology was used for pre-treatment diagnosis in preference to pathology since this would limit tissue sampling-related damage to the cervix as this can affect the natural history of cervical lesions which may, in turn, affect treatment outcome. Furthermore, since the study was primarily aimed at assessing the tolerability of a new treatment, it was considered desirable to limit pre-treatment damage to the ecto-cervix. Regarding the initial diagnosis, two independent cytology reports were used and it is also very clear that a positive high-risk HPV test improves the sensitivity of detecting CIN2+.

The results of this study provide evidence which supports the claimed use of Lopimune and in particular the use of Lopimune as a locally applied therapy for HPV related pre-invasive disease of the cervix. The observation that, after a short 2 week course of treatment, >60% of women, initially diagnosed with high-risk HPV positive HSIL, returned to normal cytology within 12 weeks is remarkable and is further supported by a reduction in disease severity in others providing an overall positive response to treatment in >80% of women. It is also interesting that >50% of these patients were HPV negative after 3 months.

Analysis of histopathology at 12 weeks largely confirmed these observations but with some differences. For example, patient E02 had normal cytology and VILI and was HPV negative whereas pathology showed a small region of CIN2. E06 and E29 both showed HSIL at 12 weeks but were reported as CIN1. E07 and E13 both showed LSIL at 12 weeks but were reported as CIN1-CIN2. E08 and E21 were both cytology normal and HPV negative but were reported as CIN1. Irrespective of these differences between cytology and pathology the latter still showed that ~60% of women had no detectable neoplasia at 12 weeks and others had reduced severity of disease (CIN1) indicating a combined positive response in ~77% of women. Most significantly these rates of regression are much higher than would be predicted for untreated cases of high-risk HPV positive HSIL.

Although 32 women were identified with ASCUS/LSIL only 17 were chosen at random for enrolment on the trial since funding was only available to provide follow on a maximum of 40 patients. The treatment response of these was perhaps not as striking as for the patients with HSIL since the former is known to have a higher rate of spontaneous regression. However it is also possible that women made aware of their diagnosis of ASCUS/LSIL may have been less compliant with the treatment than those diagnosed with HSIL. Nonetheless, >60% had normal cytology at 12 weeks and pathology then confirmed absence of neoplasia in >52%. Since previous work has shown the time for natural regression of high risk HPV positive ASCUS or LSIL is usually between 12 and 24 months, the rates of regression observed with Lopimune therapy are greater than would be predicted by natural causes. Even so, it was noted that two women (E36 and E39) progressed to CIN2 over the 3 month period which may indicate that the treatment dose and regimen used in the study are sub-optimal. Indeed, the observation that some women showed a transient improvement in HPV and/or cytology at 4 weeks but then went on to develop HPV positive abnormal cytology/pathology at 12 weeks supports this conclusion (See FIG. 2 and FIGS. 3 E03, E13, E17 and E39). Most preferred treatment dose and regimens are contemplated in the description.

Regarding the different HPV genotypes present, there was no significant correlation with response to treatment for any of those identified nor was there any obvious correlation with age, type of contraception used or parity and none of the women smoked.

How does the current treatment with Lopimune compare to other non-surgical treatments for cervical dysplasia? PDT has been extensively evaluated for this purpose with a large range of response rates ranging from 0-100% for CIN and 53.4-80% eradication of HPV. Disadvantages are that PDT is physician applied with each sequential treatment typically taking several hours. Also systemic use of photosensitizers can cause problems with general skin sensitization to light. Topical application with the cytotoxic anti CMV drug Cidofovir has been used to treat CIN2/3 and showed ~60% clearance of CIN but did not eliminate HPV infection as assessed by the hybrid capture 2 assay. Direct application of the immune activator Imiquimod to the cervix has been shown to have some effect against CIN and HPV infections both before and after LEEP although the treatment is continued for >8 weeks and the side effects can be quite severe. A recent study of topical application of the cytotoxic drug 5FU to the cervix showed this to be >90% effective against CIN2 lesions in young women aged 18-29 although this was physician applied and the treatment period lasted 16 weeks. Furthermore, there are issues related to the safety of applying potent DNA and RNA targeting cytotoxic agents, such as 5FU, to high-risk HPV positive pre-cancerous lesions in young women. It is well known that high-risk forms of HPV induce genetic instability in infected cells and, when this is combined with a DNA damaging agent, this may enhance the acquisition of persistent mutations in surviving cells. Clearly, these disadvantages and the potential importance of this for the development of subsequent neoplasia could only be determined by long term follow up. A review of the previously discussed alternative therapeutic approaches for the treatment of HPV related lesions was carried out by Bernard in 2004 (J Antimicrob Chemother. 2004 February; 53(2):137-9) with the conclusion that none of these are generally recommended due to side effects and limited efficacy.

The current study illustrates the usefulness of compositions comprising lopinavir and ritonavir for use as a medicament in the treatment of cancer or in the prevention of the development of cancer. Composition such as Lopimune serve as a surprisingly effective alternative to surgery for the treatment of HPV related cervical dysplasia and has many advantages over conventional treatment, including:

(a) compositions according to the invention are relatively cheap (£15.00 per patient for the current treatment protocol);
(b) compositions according to the invention are not a cytotoxic drug, do not target DNA and have very good safety profile with a current license for the long-term systemic treatment of pregnant women and children; and (c) compositions according to the invention can be self-applied and, in principle, treatment can be repeated many times since no acute adverse reactions were reported; and (d) positive antineoplastic/antiviral effects were clearly evident even as early as 4 weeks post start of treatment.

All of these factors combine to support the usefulness of the claimed invention.

Summary 821 women were recruited at Kenyatta National Hospital's Family Planning and Gynaecology Outpatients Clinics and tested for HIV, HPV (Cervista®) together with both conventional and liquid based cervical cytology (LBC—ThinPrep®). Women identified as HIV negative and HPV positive with high-grade squamous intraepithelial lesions (HSIL), atypical squamous cells of undetermined significance (ASCUS) and low-grade squamous intraepithelial lesions (LSIL) were enrolled on the trial and examined by colposcopy. They were then given a 2 week course of 1 capsule of Lopimune (CIPLA) twice-daily, self-applied as a vaginal suppository. Colposcopy, HPV testing and LBC were repeated at 4 and 12 weeks post-start of treatment with a final punch biopsy at 3 months for histology.

Out of 821 screened, 16 (1.95%) of women tested HIV positive. Of the remaining 805, 164 (20.4%) were positive for high-risk HPV of which 28 (17.1%) had HSIL, 11 (6.7%) LSIL, 21 (12.8%) ASCUS and 5 (3.0%) were diagnosed with ICC. Of these, Lopimune was given to 23 women with HSIL and 17 women with ASCUS/LSIL cytology. Post-treatment cytology at 12 weeks on women initially diagnosed with HSIL, showed 14/22 (63.6%) had no dysplasia and 4/22 (18.2%) were either LSIL or ASCUS demonstrating a combined positive response in 81.8% of women. HPV was no longer detected in 12/23 (52.2%) of women. Histology at 12 weeks showed absence of neoplasia in 13/22 (59.1%) of cases and 4/22 (18.2%) had low-grade cervical intraepithelial neoplasia (CIN1) demonstrating a combined positive response in 77.3% of women. High-grade neoplasia (CIN2-3) was found in 4/22 (18.2%) and 1/22 had a high grade glandular cell neoplasia (hCGIN). A curative treatment response was also seen for women diagnosed with ASCUS/LSIL cytology prior to treatment. These data are supported by colposcopic images which show regression of cervical lesions and no adverse reactions were reported.

These results further exemplify that compositions according to the invention serve as a self-applied therapy for HPV infection and related cervical lesions. Since there were no adverse events or detectable post-treatment morbidity, unlike surgery, this treatment may be repeated many times.

Example 3—Treatment with Lopimune Eliminates Low Risk HPV 6 and HPV 11 Genomic DNA from Cervical Smears Samples from subjects in the trials described in Example 1 and Example 2 were analysed to examine whether or not Lopimune eliminated HPV from subjects.

Use of Endpoint Duplex PCR to Detect HPV 6 & 11 Viral DNA Before and after Treatment with Lopimune:

HPV 6 & 11 are low-risk types of HPV which are the most common cause of genital warts. In order to identify specific HPV genotypes 6 and 11, duplex PCR assays were designed and optimized to simultaneously detect viral L1 or L2 plus E6 and E7 ORFs. A hot-start PCR kit was used as recommended by the manufacturer (Promega, Southampton, UK). The PCR mixtures consisted of 10 µl of 5× Green GoTaq® Flexi Buffer, 3.0 mM MgCl$_2$, 0.2 mM dNTPs, 0.1 µM of each primer, 1.25 unit GoTaq® DNA Polymerase and 50 ng of genomic DNA extracted from test ThinPrep® liquid based cytology (LBC) smear samples or HPV6/11 positive controls, giving a 50 µl reaction volume. The housekeeping gene Beta-2-microglobulin (B2M) was used as a sample DNA quality control and PCR was carried out using the above reaction mixture with 0.2 µM of each B2M primer up to a volume of 50 µl. All reactions were set up using a Veriti™ Thermal Cycler (Applied Biosystems, Paisley, UK) with the conditions and primers indicated in Table 7. The PCR products were separated by 2.5% agarose gel electrophoresis, stained with ethidium bromide and examined/photographed under UV light.

TABLE 7

Primers and PCR Conditions Used for HPV6 & 11 genotyping

| Primer ID | Oligonucleotide Sequence | Amplimer Size (bp) | PCR Parameters |
| --- | --- | --- | --- |
| SEQ ID NO 1: 6E6/7F | 5'-CTAATTCGGTGCTACCTGTGTCA-3' | 262 | 95° C. × 2 min 8 cycles: 94° C. × 45S, 60° C.-1° C./cycle × 45S, 72° C. × 45S; 35 cycles: 94° C. × 45S, 58° C. × 45S, 72° C. × 45S; 72° C. × 7 min |
| SEQ ID NO 2: 6E6/7R | 5'-GAATCTTGTCCGTCCACTTCGT-3' | | |
| SEQ ID NO 3: 6L1F | 5'-GACTCGTCTCTTTTCGATCCCACA-3' | 111 | |
| SEQ ID NO 4: 6L1R | 5'-TAGGAAAGGATGTCCACTTACACCC-3' | | |
| SEQ ID NO 5: 11E6/7F | 5'-GTGTGCCTGTTGCTTAGAACTGCA-3' | 357 | 95° C. × 2 min 8 cycles: 94° C. × 45S, 61° C.-1° C./cycle × 45S, 72° C. × 45S; 35 cycles: 94° C. × 45S, 57° C. × 45S, 72° C. × 45S; 72° C. × 7 min |
| SEQ ID NO 6: 11E6/7R | 5'-CTTGTCCACCTCATCTTCTGAGCT-3' | | |
| SEQ ID NO 7: 11L1/DF | 5'-CCTCCACCAAATGGTACACTGGAG-3' | 210 | |
| SEQ ID NO 8: 11L1/2R | 5'-CCGTCCTCGATATCCACTTTGC-3' | | |

Results

Figure 6:
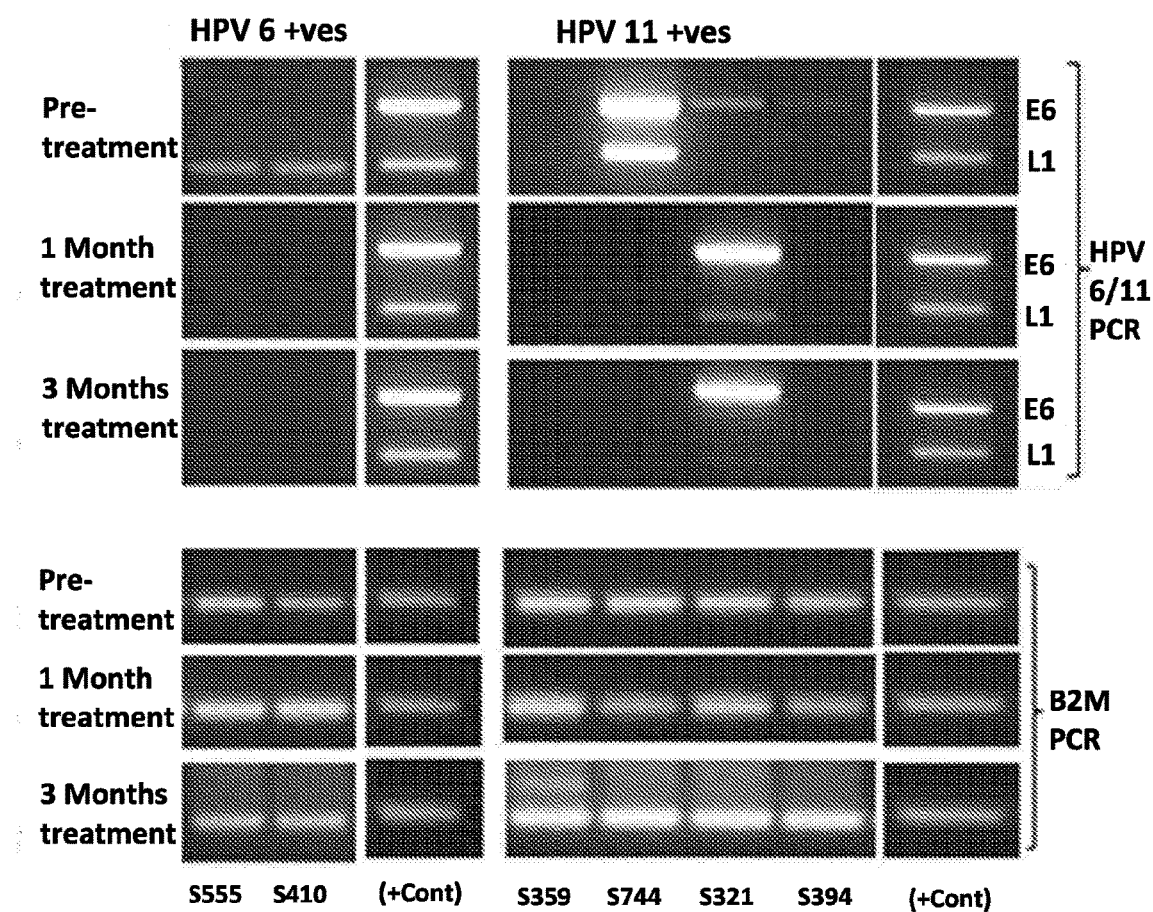
FIG. 6, illustrates an agarose gel electrophoresis of ethidium bromide stained low-risk HPV 6 or HPV 11 specific PCR products amplified from DNA extracted from LBC smears obtained from patients diagnosed with high-risk HPV positive cervical dysplasia both before and after treatment with Lopimune.

FIG. 6 shows agarose gel electrophoresis of ethidium bromide stained low-risk HPV 6 or 11 specific PCR products amplified from DNA extracted from LBC smears obtained from patients diagnosed with high-risk HPV positive cervical dysplasia both before and after treatment with Lopimune. It can be seen that two samples (S555 & S410) were positive for HPV 6 and four (S359, S744, S321, S394) for HPV 11 DNA prior to treatment giving a total of 6 patients infected with low-risk virus. (Note: The duplex assay used simultaneously detects E6/E7 and L1 but a signal with either one or the other, or both, is classed as positive).

One month post-start of treatment, 4 patients (S555, S410, S744, S394) that were positive for low-risk HPV had become negative. Although weak, the L1 signal which was still visible in S359 at one month became absent at 3 months which indicates that out of 6 patients infected with low-risk virus, only one (S321) failed to clear the infection after treatment with Lopimune. These data show that Lopimune has activity against low-risk genital wart associated forms of HPV.

These data illustrate that treatment with Lopimune eliminates Low Risk HPV 6 & 11 Genomic DNA from Cervical Smears. This confirms that treatments according to the invention are particularly effective for treating, or preventing the development of, cancerous conditions associated with HPV infection (e.g many cervical cancers). Furthermore these data illustrate that treatments according to the invention are effective for treating other conditions associated with HPV infection such as benign proliferative disorders (e.g. genital warts) as well as cancers.

Example 4—Colorimetric Analysis of Cell Growth

A colorimetric analysis of cell growth was performed to investigate the activity of lopinavir and ritonavir against HPV positive cervical carcinoma cell lines when administered either separately or combined.

SiHa cells were grown in RPMI plus 10% FBS and HeLa in DMEM plus 10% FBS. These were seeded at 2000 cells/well for HeLa and 5000 cells/well for SiHa in triplicate into standard tissue culture grade 96 well plates and incubated overnight at 37° C./5% $CO_2$ Different concentrations and ratios of lopinavir and ritonavir were then added in an identical volume of DMSO, plus a DMSO only control, and the incubation continued for 0, 24, 48 and 72 hours. At each time point 20 µl of CellTitre 96® AQ reagent (Promega) was then added to three separate wells per data point and the absorbance ($OD_{490}$) read after 1 hour at 37° C. The CellTitre 96® AQ reagent is a water soluble MTS formazan version of the well-known MTT reagent which produces a colorimetric readout that is directly proportional to the number of viable cells present.

Results

Figure 7A:
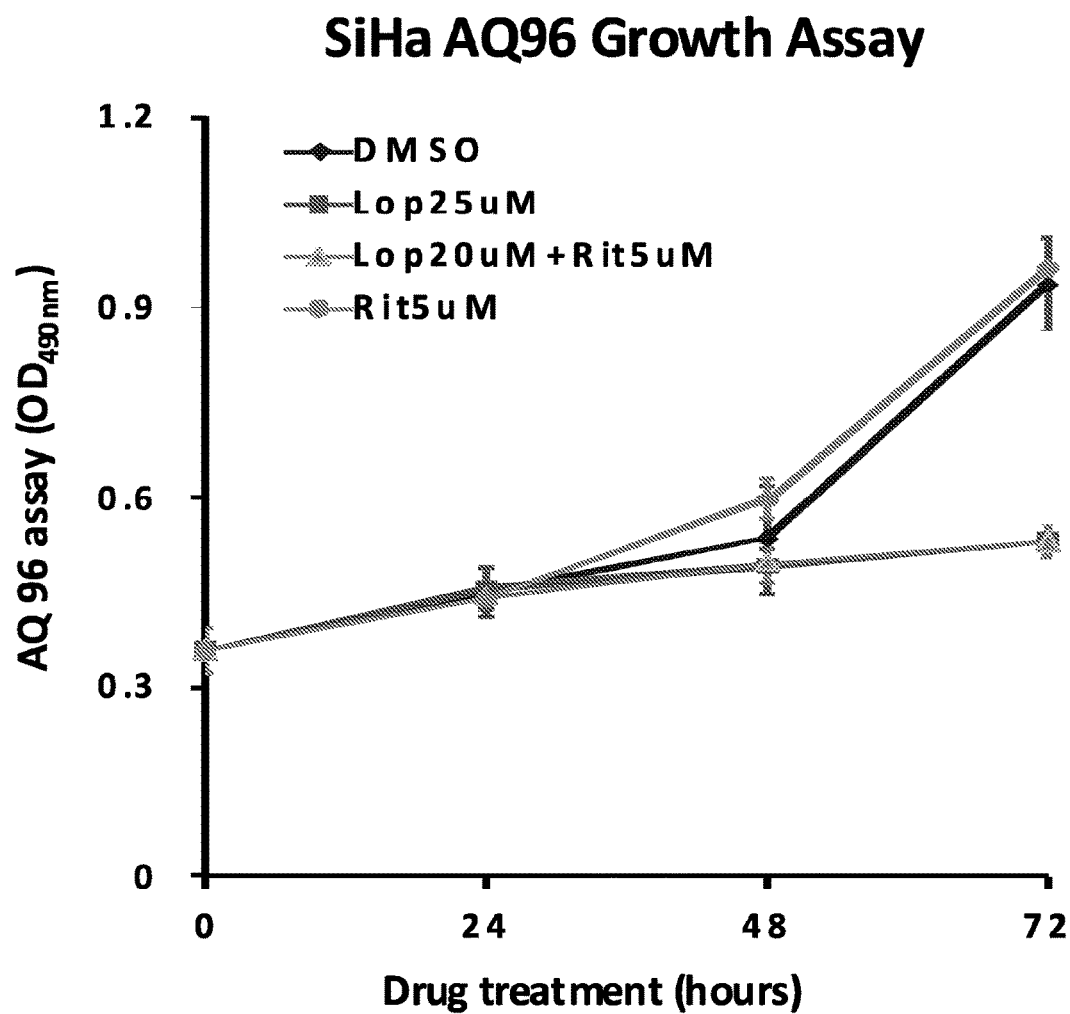
FIGS. 7A-7B, illustrate the results of AQ96 Growth Assays for SiHa (A) and Hela (B) cells.
Figure 7B:
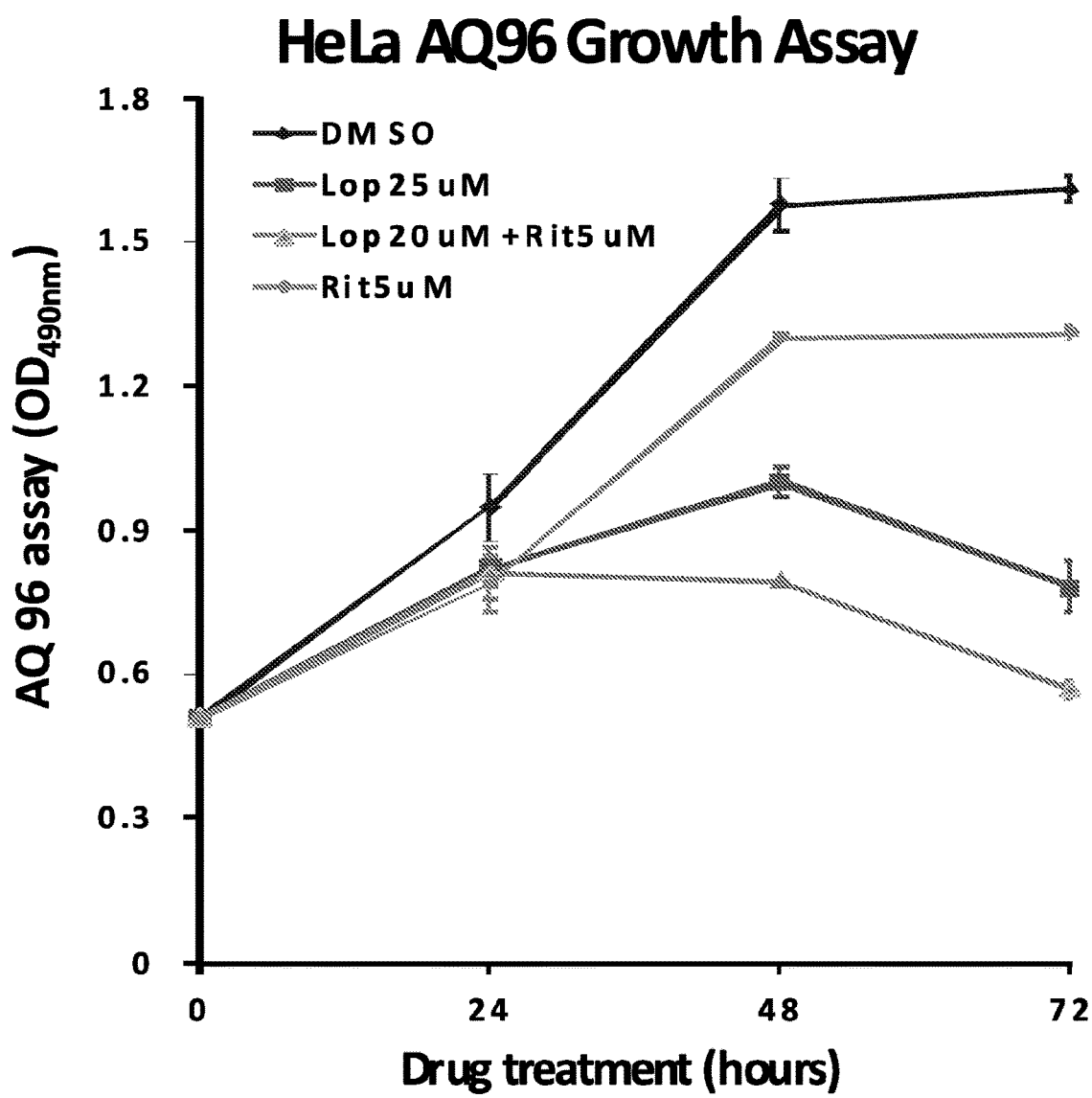

The results of these experiments are presented in FIG. 7 for SiHa (FIG. 7A) and Hela (FIG. 7B) cells. SiHa are HPV16 positive whereas HeLa cells are HPV18 positive cervical carcinoma cell lines and the DMSO control growth curves show that the HeLa cells have a more rapid growth rate than do SiHa. For SiHa cells it can be seen that 20 µM lopinavir plus 5 ritonavir has the same inhibitory effect on cell growth as 25 µM lopinavir, with 5 µM ritonavir having no effect. With HeLa cells, it can be seen that 20 µM lopinavir plus 5 µM ritonavir was more growth inhibitory than either 25 µM lopinavir or 5 µM ritonavir when these were applied as single agents, which illustrates that the combination is more effective at inhibiting growth than either compound applied as a single agent. However, although this method implies that the additive combination of lopinavir and ritonavir is as effective at killing cells as 100% lopinavir in SiHa and more effective in HeLa cells, it does not directly measure cell death. For this reason the activity of these compounds was also evaluated by methods which directly measure either apoptosis or total cell death (see Example 5).

Example 5—Analysis of Apoptosis Using Dual Staining with V450 Annexin V and Propidium Iodide Methods Staining with V450 Annexin V (BD Biosciences) was used to analyse the percentage of cells within a population that are actively undergoing apoptosis. Propidium Iodide (PI) is a standard DNA-staining flow cytometric viability probe and is used to distinguish viable from nonviable cells. Cells that stain positive for V450 Annexin V and negative for PI are undergoing apoptosis. Cells that stain positive for both V450 Annexin V and PI are either in the end stages of apoptosis, are undergoing necrosis, or are already dead. Cells that stain negative for both V450 Annexin V and PI are alive and not undergoing measurable apoptosis.

HeLa cells are notoriously robust and yet the previously discussed CellTitre 96® AQ assays showed they underwent pronounced growth inhibition when treated with lopinavir and ritonavir combined. For this reason these cells were chosen to evaluate the effects of these compounds on cell death. A 2 ml aliquot of growth medium containing 20,000 cells was seeded into each well of a 6 well plate. After 72 hrs incubation in DMEM (10% FBS and 1% L-Glutamine) at 37° C./5% $CO_2$, various concentrations and ratios of lopinavir and ritonavir were added in an identical volume of DMSO and the cells incubated for a further 48 hrs. The growth medium was removed and retained and the cells washed with PBS followed by Incubation with 1 ml of Accutase (Life Technologies, Paisley, UK, Catalog Number A11105-01) per well for 15 mins. The original growth medium was then added back to neutralise the Accutase, and this centrifuged at 1,200 rpm for 5 mins to pellet the cells and this repeated twice with cold PBS. The cell pellet was finally re-suspended in 1× binding buffer (10×=0.1 M Hepes (pH 7.4), 1.4 M NaCl, 25 mM $CaCl_2$) at a concentration of $10^6$ cell/ml. A 100 µl aliquot containing $10^5$ cells was removed and placed in a 5 ml culture tube and 5 µl of V450 Annexin V added plus 10 µl PI (50 µg/ml) added. The cells were gently mixed and incubated at room temperature for 15 min in the dark then 400 µl of 1× binding buffer was added prior to being analysed by flow cytometry using a Cyan ADP instrument (Beckman Coulter) and Summit software within one hour of the above procedure. The Annexin fluorochrome was excited using a 405 nm laser and the emission measured using a 450/50 nm bandpass filter. The PI was excited using a 488 nm laser and the emission detected using a 613/20 nm bandpass filter. The data was gated to select single cells using a plot of forward scatter against pulse width, and to exclude debris using forward scatter plotted against side scatter. All cytometry assays shown were the result of three separate cultures and intra-assay variability was also assessed by repeating the same drug treatment assay (1:1 Lop/Rit) three times. Unstained cells and cells stained separately with either V450 Annexin V or PI were used as controls to optimise compensation and gating of the cytometer.

Results

Figure 8:
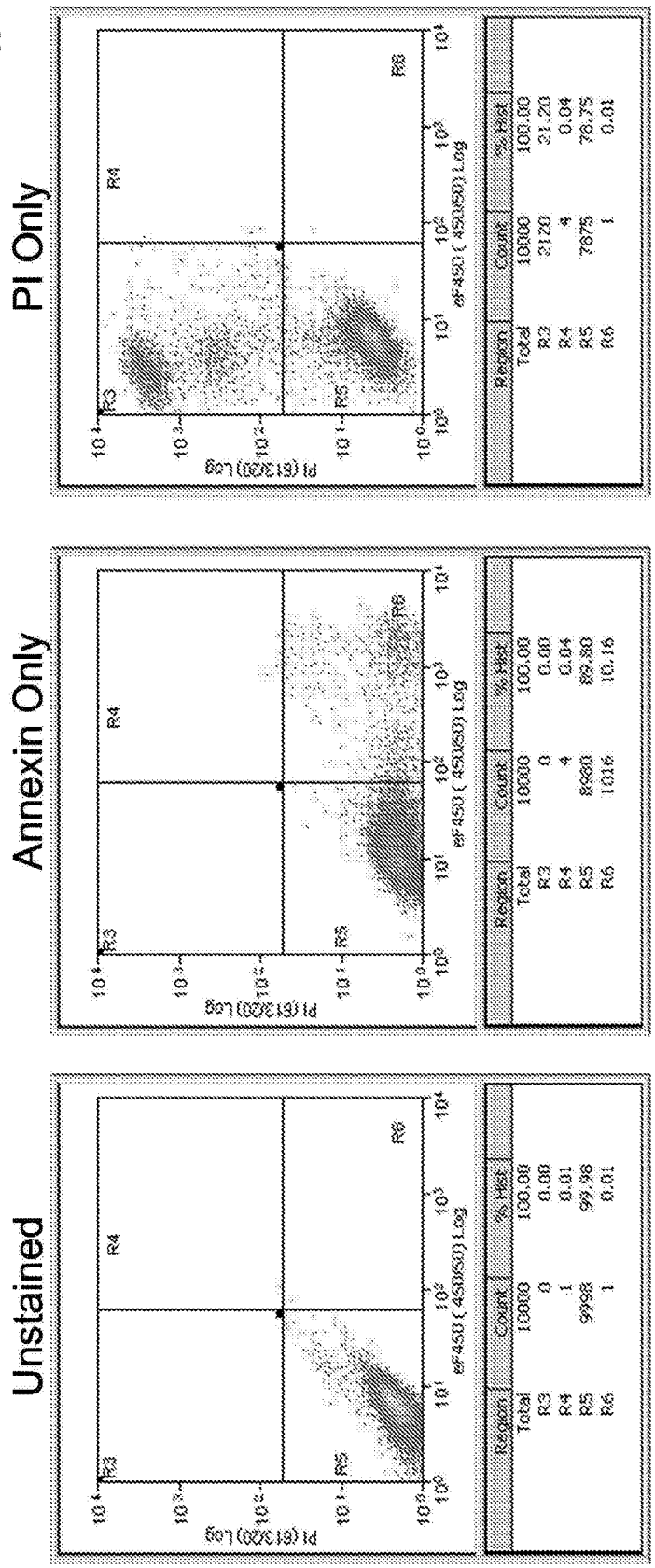
FIG. 8, illustrates scatter plot profiles of unstained, annexin-only and PI-only stained HeLa cells used to optimise the cytometer and set gates appropriately. This also showed that very little background was observed in the R4 quadrant where advanced stage apoptotic cells should be detected.

Scatter Plots Following Analysis in a Cell Cytometer:

The scatter plots of FIG. 8 show profiles of unstained, annexin-only and PI-only stained HeLa cells were used to optimise the cytometer and set gates appropriately. This also showed that very little background was observed in the R4 quadrant where advanced stage apoptotic cells should be detected.

The scatter plots of FIG. 9 show analysis of triplicate cultures treated with 1:1 (12.5 lopinavir (Lop)+12.5 µM ritonavir (Rit)) with an additional analysis of one culture repeated 3 times to determine the intra cytometer assay variance. (Note: Cells in the R6 quadrant are in earlier stages of apoptosis).

The scatter plots of FIG. 10 show analysis of triplicate cultures treated with 4:1 (20 Lop+5 µM Rit) plus cultures of 4 percentage point differences which indicated that the scatter plots have a high degree of reproducibility.

Figure 13:
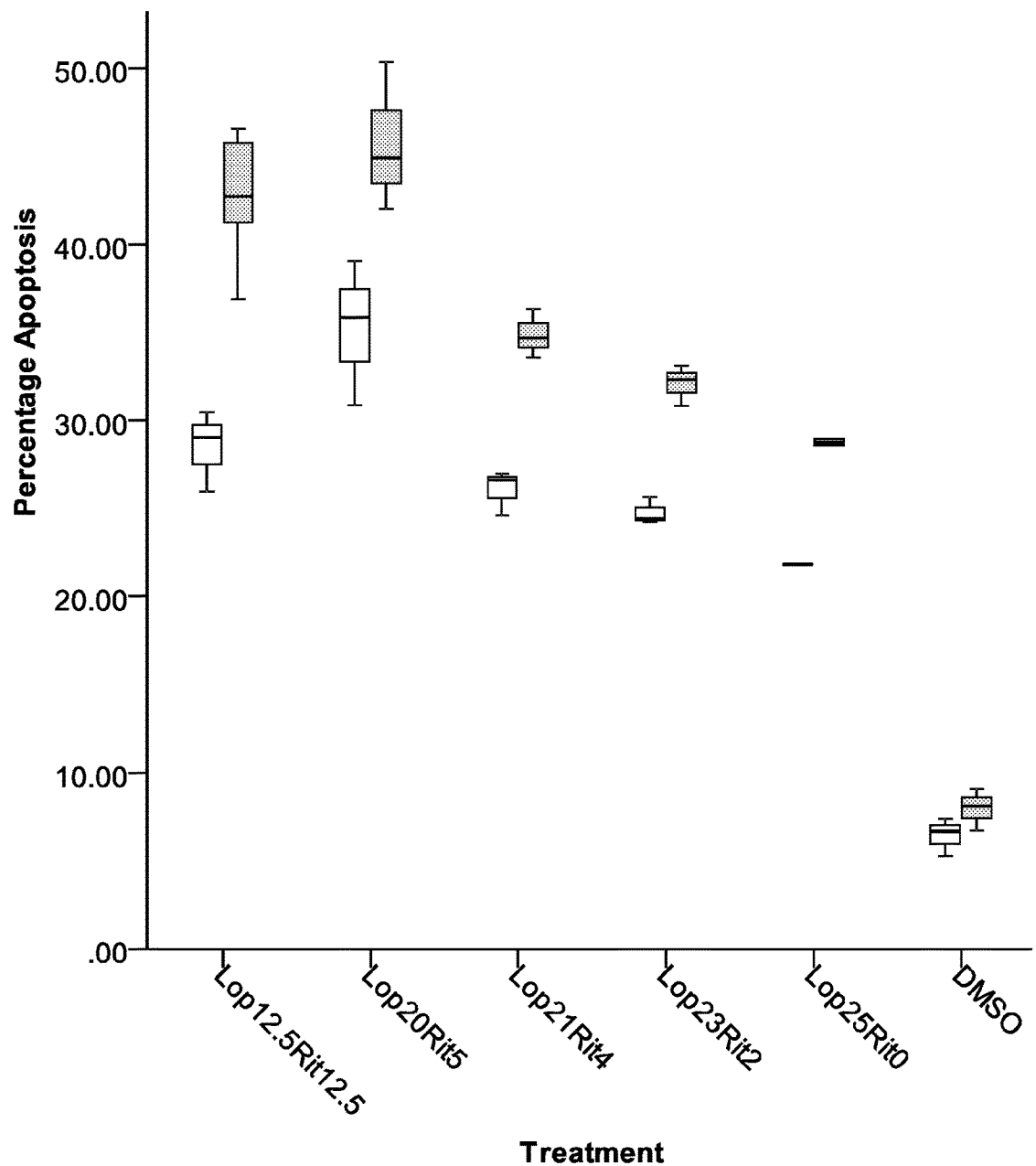
FIG. 13 is a box plot comparing the effects of the various drug treatments on levels of apoptosis.

Comparison of Percentage Apoptotic Cells Between Treatments:

FIG. 13 is a box plot showing comparison of the effects of the various drug treatments on the levels of late apoptosis (white boxes R4) and early+late apoptosis (shaded boxes R6+R4) observed in these cultures. It can be seen that 4:1 (20 µM Lop+5 µM Rit) has the highest level of apoptosis followed by 1:1 (12.5 µM Lop+12.5 µM Rit). Reducing the amount of ritonavir below 5 µM and increasing amounts of lopinavir caused a reduction in the amount of apoptosis observed. These results indicate that, with a total dose of 25 the optimal drug ratio lies between 1:1 and 4:1 lopinavir/ritonavir. Furthermore, 25 µM lopinavir as a single agent was less effective than any of the combination treatments Statistical Analysis Table 8 illustrates an α level of 0.05; the replicate readings are acceptable; and the 95% confidence intervals do not pass 0. The means are therefore suitable for ANNOVA which showed significant difference between sample means (table 9). F score of 59.252 and a p value of $1.4 \times 10^{-7}$ (ie $<\alpha 0.05$)

TABLE 8

| R4 gate | Mean | Std. Deviation | Std. Error | 95% Confidence Interval for Mean | | Min | Max |
|---|---|---|---|---|---|---|---|
| | | | | Lower Bound | Upper Bound | | |
| DMSO | 6.4233 | 1.07472 | .62049 | 3.7536 | 9.0931 | 5.25 | 7.36 |
| Lop12.5Rit12.5 | 28.4967 | 2.29740 | 1.32640 | 22.7896 | 34.2037 | 25.97 | 30.46 |
| Lop20Rit5 | 35.2500 | 4.13668 | 2.38831 | 24.9739 | 45.5261 | 30.85 | 39.06 |
| Lop21Rit4 | 26.0733 | 1.28722 | .74318 | 22.8757 | 29.2710 | 24.60 | 26.98 |
| Lop23Rit2 | 24.7800 | .79379 | .45829 | 22.8081 | 26.7519 | 24.23 | 25.69 |
| Lop25Rit0 | 21.8000 | .01414 | .01000 | 21.6729 | 21.9271 | 21.79 | 21.81 |
| Total | 23.9218 | 9.49713 | 2.30339 | 19.0388 | 28.8047 | 5.25 | 39.06 | treated with decreasing amounts of ritonavir (21 µM Lop+4 Rit and 23 µM Lop+2 µM Rit).

Figure 11:
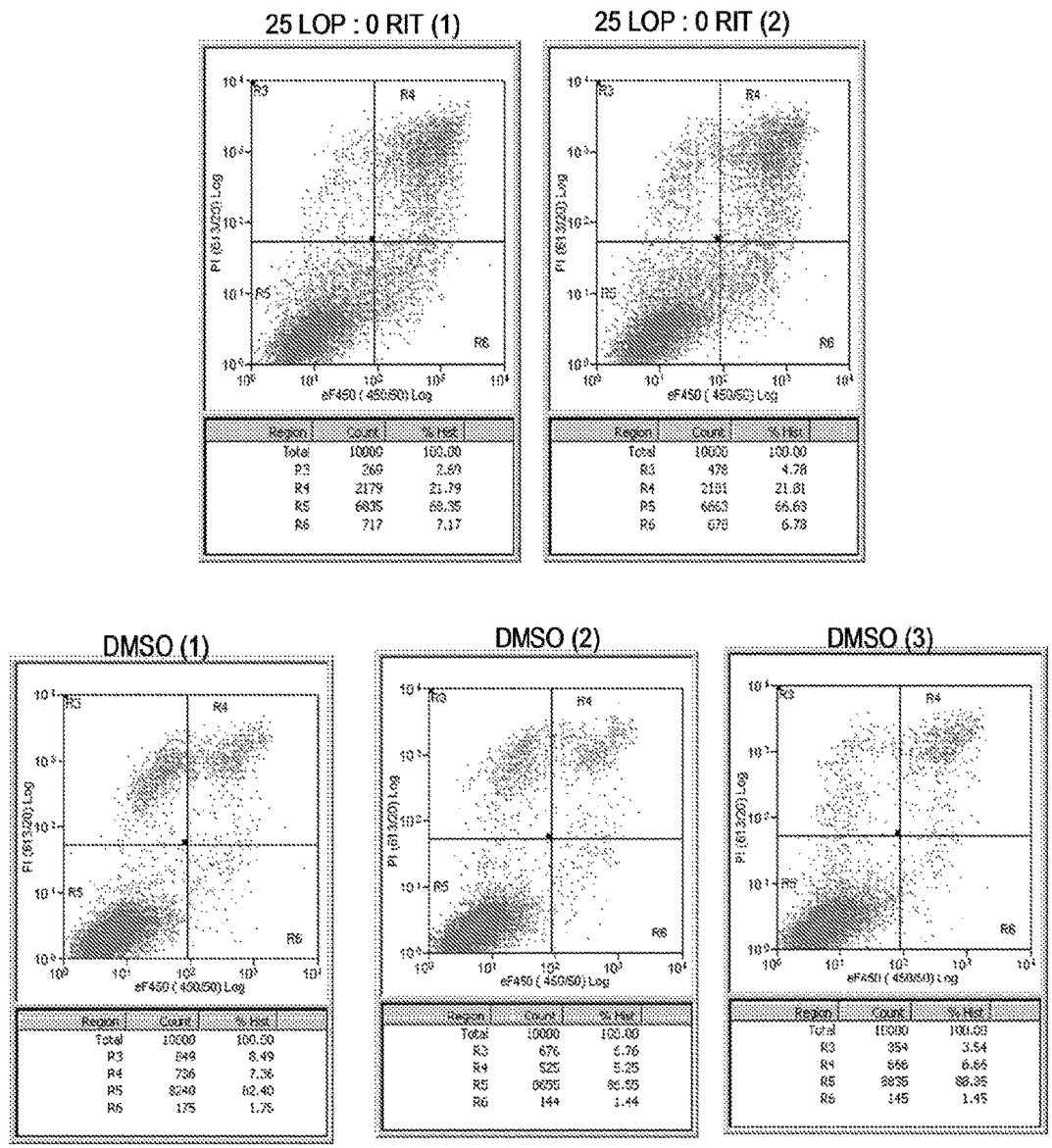
FIG. 11, illustrates scatter plot showing duplicate cultures treated with 25 µM lopinavir as a single agent and triplicate cultures treated with same amount of DMSO used for all the drug assays shown.

The scatter plots of FIG. 11 show duplicate cultures treated with 25 µM Lop as a single agent and triplicate cultures treated with same amount of DMSO used for all the drug assays shown.

Figure 12:
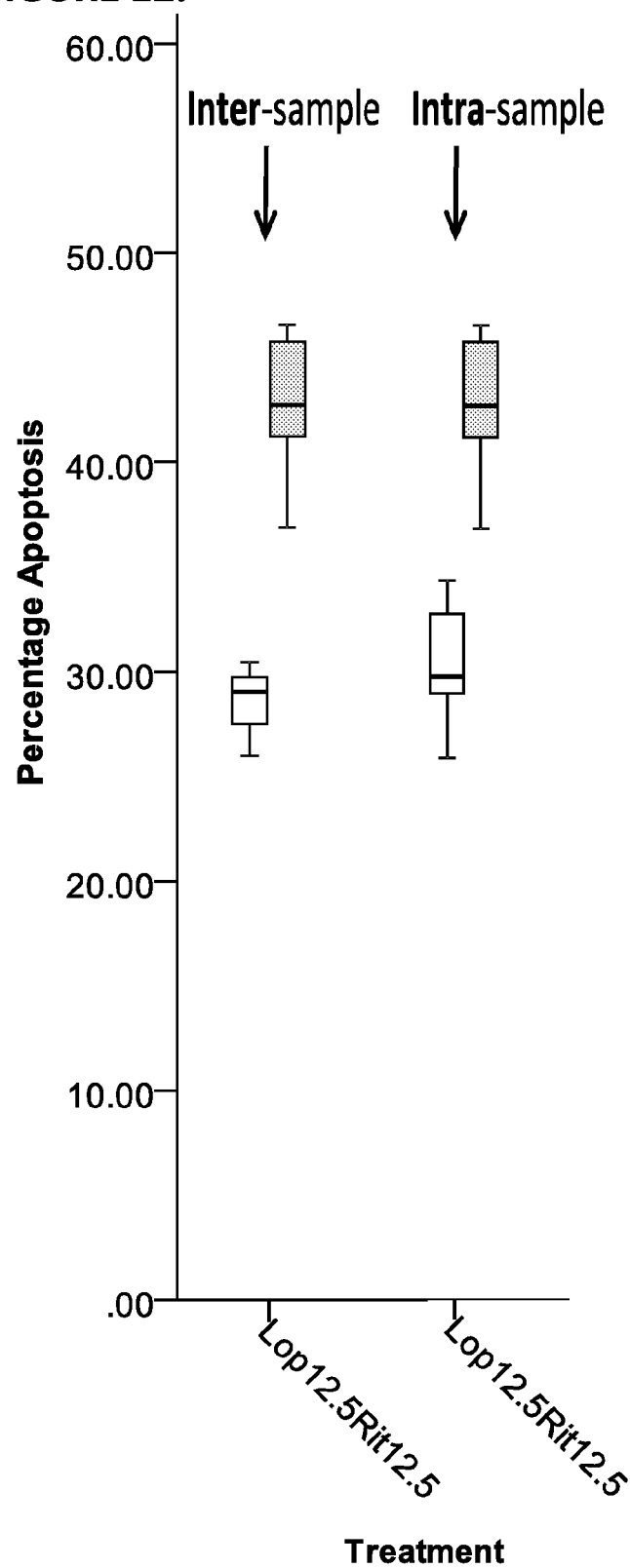
FIG. 12 is a graph illustrating the analysis of intra and inter sample variance which occurred within and between flow cytometry apoptotic assays carried out on 1:1 (12.5 µM Lop+12.5 µM Rit) treatments.

Analysis of Inter and Intra Sample Variance:

FIG. 12 is a graph showing the analysis of intra and inter sample variance which occurred within and between the flow cytometry apoptotic assays carried out on 1:1 (12.5 µM Lop+12.5 µM Rit) treatments. The white box plots represent the percentage of cells found in quadrant R4 (Late stage apoptosis) whereas the shaded box plots represent the percentage found in R6+R4 (combined early and late stage apoptosis). Intra-sample readings demonstrated a maximum

TABLE 9

| | Sum of Squares | df | Mean Square | F | Sig. |
|---|---|---|---|---|---|
| Between Groups | 1391.462 | 5 | 278.292 | 59.252 | 0.000000139935051 |
| Within Groups | 51.665 | 11 | 4.697 | | |
| Total | 1443.127 | 16 | | | |

Table 10 illustrates that Dunnet post-hoc shows that all treatments are significantly different to DMSO (p value range: $1.9 \times 10^{-5}$ to $1.8 \times 10^{-8}$).

TABLE 10

| | Treatment Condition | | Mean Difference | Std. Error | Sig. | 95% Confidence Interval | |
|---|---|---|---|---|---|---|---|
| | | | | | | Lower Bound | Upper Bound |
| Dunnett t (>control)[b] | Lop12.5Rit12.5 | DMSO | 22.07333* | 1.76952 | 0.000000 | 17.5805 | |
| | Lop20Rit5 | DMSO | 28.82667* | 1.76952 | 0.000000 | 24.3338 | |
| | Lop21Rit4 | DMSO | 19.65000* | 1.76952 | 0.000001 | 15.1571 | |
| | Lop23Rit2 | DMSO | 18.35667* | 1.76952 | 0.000001 | 13.8638 | |
| | Lop25Rit0 | DMSO | 15.37667* | 1.97838 | 0.000019 | 10.3535 | |

Bonferonni post-hoc analysis (Table 11) also shows that all treatments are significantly different to DMSO (expected, not shown) p value range: $1.29 \times 10^{-4}$ to $7.14 \times 10^{-8}$.

TABLE 11

| | Bonferonni Treatment Condition | | | | 95% Confidence Interval | |
|---|---|---|---|---|---|---|
| | | Mean Difference | Std. Error | Sig. | Lower Bound | Upper Bound |
| Lop12.5Rit12.5 | Lop20Rit5 | −6.75333* | 1.76952 | 0.042907 | −13.3506 | −.1561 |
| Lop20Rit5 | Lop12.5Rit12.5 | 6.75333* | 1.76952 | 0.042907 | .1561 | 13.3506 |
| | Lop21Rit4 | 9.17667* | 1.76952 | 0.004514 | 2.5794 | 15.7739 |
| | Lop23Rit2 | 10.47000* | 1.76952 | 0.001509 | 3.8727 | 17.0673 |
| | Lop25Rit0 | 13.45000* | 1.97838 | 0.000444 | 6.0740 | 20.8260 |
| Lop23Rit2 | Lop20Rit5 | −10.47000* | 1.76952 | 0.001509 | −17.0673 | −3.8727 |
| Lop25Rit0 | Lop20Rit5 | −13.45000* | 1.97838 | 0.000444 | −20.8260 | −6.0740 |

Example 6—Analysis of Total Cell Death by Trypan Blue Staining

Methods

Unlike the previous Annexin V/PI method, Trypan blue staining does not detect cells in the early stages of programmed cell death or distinguish between apoptotic and necrotic cell death.

In similar fashion to the Annexin V/PI assay, 2 ml aliquots of growth medium containing 20,000 cells were seeded into 6 well plates. After 72 hrs incubation in DMEM (10% FBS and 1% L-Glutamine) at 37° C./5% $CO_2$, various concentrations and ratios of lopinavir and ritonavir were added in an identical volume of DMSO and the cells incubated for a further 48 hrs. The growth medium was removed and retained and the cells washed with PBS followed by Incubation with 1 ml of Accutase (Life Technologies, Paisley, UK, Catalog Number A11105-01) per well for 15 mins. The original growth medium was then added back to neutralise the Accutase, and this centrifuged at 1,200 rpm for 5 mins to pellet the cells which were then re-suspended in PBS. An equal volume of 0.4% w/v Trypan blue solution (Sigma) was added and live/dead cells counted using a haemocytometer. All assays were the result of three separate cultures and all cell counts were repeated in triplicate.

Results

Figure 14:
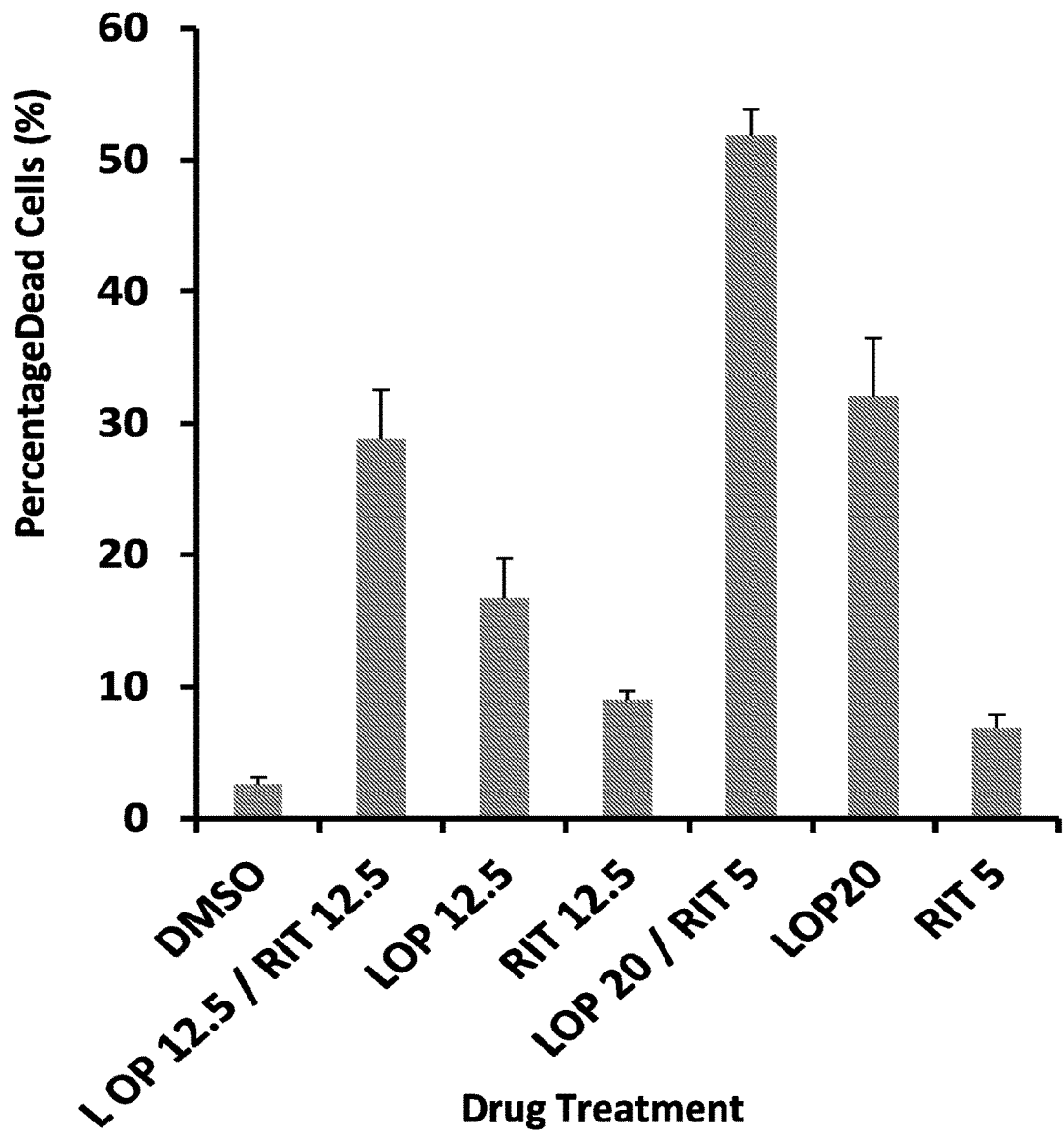
FIG. 14 illustrates total cell death in Hela cell as measured by Trypan blue dead cell assay.

FIG. 14 illustrates total cell death in Hela cells as measured by the Trypan Blue dead cell assay. If the DMSO percentage background cell death is subtracted from the various drug treatments, it can be seen that the combination of the 4:1 (20 µM lopinavir plus 5 µM ritonavir) exhibits synergy whereby this was more effective at inducing cell death (49.18%) than the sum of both compounds (33.66%) when these were administered separately. Dropping the ratio of the two drugs to 1:1 (12.5 µM Lopinavir plus 12.5 µM ritonavir) was somewhat less effective at inducing cell death than the 4:1 ratio and did not show quite the same level of synergy. Accordingly a ratio of 4:1 (lopinavir:ritonavir) represents a preferred ratio for compositions used according to the invention.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

The disclosures of each patent, patent application, and publication cited or described in this document are hereby incorporated herein by reference, in its entirety

EMBODIMENTS

The following list of embodiments is intended to complement, rather than displace or supersede, the previous descriptions.

Embodiment 1

A composition comprising lopinavir, with or without, ritonavir for use as a medicament in the treatment of cancer or benign proliferative disorders (warts) or in the prevention of the development of cancer.

Embodiment 2

The composition according to Embodiment 1 comprising lopinavir and ritonavir.

Embodiment 3

The composition according to Embodiments 1 or 2 used to prevent the development of cancer.

Embodiment 4

The composition according to Embodiment 3 used in a dose that is effective for treating a Human Papilloma Virus (HPV) infection with or without attendant abnormal pathology.

Embodiment 5

The composition according to any preceding Embodiments wherein the medicament is used to treat or prevent the development of early stage neoplasias.

Embodiment 6

The composition according to any preceding Embodiments wherein the medicament is used to treat or prevent the development of HPV related cervical, vulval, vaginal, penile, anal, oral, laryngeal neoplasias and/or warts.

Embodiment 7

The composition according to Embodiment 6 wherein the medicament is used to treat or prevent the development of cervical neoplasias.

Embodiment 8

The composition according to any preceding Embodiment wherein the medicament is formulated for topical application.

Embodiment 9

The composition according to any preceding Embodiment wherein the medicament comprises between about 100-600 mgs of lopinavir with our without between 30-175 mg of ritonavir.

Embodiment 10

The composition according to Embodiment 9 wherein the medicament comprises about 133.3 mgs of lopinavir and about 33.3 mg of ritonavir.

Embodiment 11

The composition according to any preceding Embodiment wherein the medicament is administered either once or twice daily.

Embodiment 12

The composition according to any preceding Embodiment wherein the medicament is administered for a period of between 7 and 21 days.

Embodiment 13

The composition according to Embodiment 12 wherein the medicament is administered for second or further period of between 7 and 21 days.

Embodiment 14

The composition according to Embodiment 13 wherein the medicament is administered in a treatment regimen of a first period of 14-21 days; followed by a period of 1-14 days without treatment; and then followed by a second period of 14-21 days.

Embodiment 15

A composition comprising lopinavir for use as a medicament in the treatment of cancer or benign proliferative disorders (warts) or in the prevention of the development of cancer.

Embodiment 16

A pharmaceutical composition that is formulated for topical application comprising a therapeutically effective amount of lopinavir or a therapeutically effective amount lopinavir and ritonavir in a pharmaceutically acceptable vehicle.

Embodiment 17

The pharmaceutical composition of Embodiment 16, comprising a synergistic amount of lopinavir and ritonavir.

Embodiment 18

The pharmaceutical composition of Embodiment 17, wherein the synergistic amount of lopinavir and ritonavir is from about 1:1 to about 4:1 lopinavir to ritonavir.

Embodiment 19

The pharmaceutical composition of Embodiment 17, wherein the synergistic amount of lopinavir to ritonavir is from about 1:1 to less than 4:1 lopinavir to ritonavir.

Embodiment 20

The pharmaceutical composition of any one of Embodiments 16-19, wherein the pharmaceutical composition is formulated for intravaginal delivery.

Embodiment 21

The pharmaceutical composition of Embodiment 20, wherein the formulation comprises a gel, cream, ointment, lotion, ovule, soft capsule, suppository, pessary, or any combination thereof.

Embodiment 22

The pharmaceutical composition of any one of Embodiments 16-20, wherein the formulation is substantially free of pigments, dyes, and inks.

Embodiment 23

A method of treating a patient having an HPV related dysplasia of the cervix comprising administering to said patient a therapeutically effective dose of the pharmaceutical composition of any one of claims 16-22.

Embodiment 24

The method of Embodiment 22, wherein the pharmaceutical composition reduces the severity of the HPV related dysplasia.

Embodiment 25

The method of Embodiment 24, wherein the severity of the HPV is reduced from CIN3 to CIN2, from CIN3 to CIN1, from CIN3 to HPV negative, from CIN2 to CIN1, from CIN2 to HPV negative, or from CIN1 to HPV negative.

Embodiment 26

The method of Embodiment 25, wherein the severity is reduced from about 4 weeks to about 52 weeks following administering said composition.

Embodiment 27

The method according to any one of Embodiments 23 or 26, wherein the patient has a cervical cytology of high grade squamous intraepithelial lesion (HSIL), atypical squamous cells of undetermined significance (ASCUS), or low grade squamous intraepithelial lesion (LSIL).

Embodiment 28

The method of Embodiment 27, wherein the composition reduces the cervical cytology.

Embodiment 29

The method of Embodiment 28, wherein the cervical cytology is reduced from HSIL to a normal cytology, from HSIL to ACSUS, from HSIL to LSIL, from ACSUS to a normal cytology, or from LSIL to a normal cytology.

Embodiment 30

The method of Embodiment 29, wherein the cervical cytology is reduced from about 4 weeks to about 52 weeks following administering said composition.

Embodiment 31

The method according to any one of Embodiments 23-30, wherein the composition is administered twice daily for 14 days.

Embodiment 32

The method of any one of Embodiments 23-31, wherein the composition induces apoptosis of HPV infected cells.

What is claimed:

1. A pharmaceutical composition that is formulated for topical application comprising a therapeutically effective amount lopinavir and ritonavir in a pharmaceutically acceptable vehicle.

2. The pharmaceutical composition of claim 1, comprising a synergistic amount of lopinavir and ritonavir.

3. The pharmaceutical composition of claim 2, wherein the synergistic amount of lopinavir and ritonavir is from about 1:1 to about 4:1 lopinavir to ritonavir.

4. The pharmaceutical composition of claim 2, wherein the synergistic amount of lopinavir to ritonavir is from about 1:1 to less than 4:1 lopinavir to ritonavir.

5. The pharmaceutical composition of claim 1, wherein the pharmaceutical composition is formulated for intravaginal delivery.

6. The pharmaceutical composition of claim 5, wherein the formulation comprises a gel, cream, ointment, lotion, ovule, soft capsule, suppository, pessary, or any combination thereof.

7. The pharmaceutical composition of claim 1, wherein the formulation is substantially free of pigments, dyes, and inks.

8. A method of treating a patient having an HPV related dysplasia of the cervix comprising administering intravaginally to said patient a therapeutically effective dose of the pharmaceutical composition of claim 1.

9. The method of claim 8, wherein the pharmaceutical composition reduces the severity of the HPV related dysplasia.

10. The method of claim 9, wherein the severity of the HPV is reduced from CIN3 to CIN2, from CIN3 to CIN1, from CIN3 to HPV negative, from CIN2 to CIN1, from CIN2 to HPV negative, or from CIN1 to HPV negative.

11. The method of claim 10, wherein the severity is reduced from about 4 weeks to about 52 weeks following administering said composition.

12. The method of claim 8, wherein the patient has a cervical cytology of high grade squamous intraepithelial lesion (HSIL), atypical squamous cells of undetermined significance (ASCUS), or low grade squamous intraepithelial lesion (LSIL).

13. The method of claim 12, wherein the composition reduces the cervical cytology.

14. The method of claim 13, wherein the cervical cytology is reduced from HSIL to a normal cytology, from HSIL to ACSUS, from HSIL to LSIL, from ACSUS to a normal cytology, or from LSIL to a normal cytology.

15. The method of claim 14, wherein the cervical cytology is reduced from about 4 weeks to about 52 weeks following administering said composition.

16. The method of claim 8, wherein the composition is administered twice daily for 14 days.

17. The method of claim 8, wherein the composition induces apoptosis of HPV infected cells.

18. A method of treating cancer or benign proliferative disorders of the vagina or cervix, or reducing the likelihood of the development of cancer of the vagina or cervix, comprising:
    topically administering a composition comprising lopinavir with ritonavir to a subject in need thereof.

19. The method of claim 18, wherein the method reduces the likelihood of the development of cancer.

20. The method of claim 19, wherein the composition is in a dose that is effective for treating a Human Papilloma Virus (HPV) infection with or without attendant abnormal pathology.

21. The method of claim 18, wherein the method treats or reduces the likelihood of the development of early stage neoplasias.

22. The method of claim 18, wherein the method treats or reduces the likelihood of the development of HPV related cervical, vulval, vaginal, penile, anal, oral, laryngeal neoplasias and/or warts.

23. The method of claim 22 wherein the method treats or reduces the development of cervical neoplasias.

24. The method of claim 18, wherein the composition is formulated for topical application.

25. The method of claim 18, wherein the composition comprises between about 100 mg to about 600 mg of lopinavir with between about 30 mg to about 175 mg of ritonavir.

26. The method of claim 25, wherein the composition comprises about 133.3 mgs of lopinavir and about 33.3 mg of ritonavir.

27. The method of claim 18, wherein the composition is administered either once or twice daily.

28. The method of claim 18, wherein the composition is administered for a period of between 7 and 21 days.

29. The method of claim 28, wherein the composition is administered for a second or further period of between 7 and 21 days.

30. The method of claim 29, wherein the composition is administered in a treatment regimen of a first period of 14-21 days; followed by a period of 1-14 days without treatment; and then followed by a second period of 14-21 days.

31. The method of claim 18, wherein the proliferative disorders of the vagina or cervix is warts.

* * * * *

SEQUENCE LISTING

```
<160> NUMBER OF SEQ ID NOS: 8

<210> SEQ ID NO 1
<211> LENGTH: 23
<212> TYPE: DNA
<213> ORGANISM: Artificial
<220> FEATURE:
<223> OTHER INFORMATION: PCR Primer

<400> SEQUENCE: 1
ctaattcggt gctacctgtg tca                                            23

<210> SEQ ID NO 2
<211> LENGTH: 22
<212> TYPE: DNA
<213> ORGANISM: Artificial
<220> FEATURE:
<223> OTHER INFORMATION: PCR Primer

<400> SEQUENCE: 2
gaatcttgtc cgtccacttc gt                                             22

<210> SEQ ID NO 3
<211> LENGTH: 24
<212> TYPE: DNA
<213> ORGANISM: Artificial
<220> FEATURE:
<223> OTHER INFORMATION: PCR Primer

<400> SEQUENCE: 3
gactcgtctc ttttcgatcc caca                                           24

<210> SEQ ID NO 4
<211> LENGTH: 25
<212> TYPE: DNA
<213> ORGANISM: Artificial
<220> FEATURE:
<223> OTHER INFORMATION: PCR Primer

<400> SEQUENCE: 4
taggaaagga tgtccactta caccc                                          25

<210> SEQ ID NO 5
<211> LENGTH: 24
<212> TYPE: DNA
<213> ORGANISM: artificial
<220> FEATURE:
<223> OTHER INFORMATION: PCR Primer

<400> SEQUENCE: 5
```

```
gtgtgcctgt tgcttagaac tgca                                          24

<210> SEQ ID NO 6
<211> LENGTH: 24
<212> TYPE: DNA
<213> ORGANISM: Artificial
<220> FEATURE:
<223> OTHER INFORMATION: PCR Primer

<400> SEQUENCE: 6
cttgtccacc tcatcttctg agct                                          24

<210> SEQ ID NO 7
<211> LENGTH: 24
<212> TYPE: DNA
<213> ORGANISM: Artificial
<220> FEATURE:
<223> OTHER INFORMATION: PCR Primer

<400> SEQUENCE: 7
cctccaccaa atggtacact ggag                                          24

<210> SEQ ID NO 8
<211> LENGTH: 22
<212> TYPE: DNA
<213> ORGANISM: Artificial
<220> FEATURE:
<223> OTHER INFORMATION: PCR Primer

<400> SEQUENCE: 8
ccgtcctcga tatccactttt gc                                           22
```